(12) United States Patent
Tani et al.

(10) Patent No.: US 9,643,940 B2
(45) Date of Patent: May 9, 2017

(54) AMINE SALT AND CRYSTALS THEREOF

(71) Applicant: ONO PHARMACEUTICAL CO., LTD., Osaka-shi, Osaka (JP)

(72) Inventors: Kousuke Tani, Osaka (JP); Akihiro Kinoshita, Osaka (JP); Keisuke Hanada, Osaka (JP); Yoshiyuki Aratani, Sakai (JP); Takahiro Nekado, Osaka (JP); Atsushi Shimabukuro, Osaka (JP)

(73) Assignee: ONO PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 14/424,215

(22) PCT Filed: Aug. 30, 2013

(86) PCT No.: PCT/JP2013/073442
§ 371 (c)(1),
(2) Date: Feb. 26, 2015

(87) PCT Pub. No.: WO2014/034902
PCT Pub. Date: Mar. 6, 2014

(65) Prior Publication Data
US 2015/0218114 A1    Aug. 6, 2015

(30) Foreign Application Priority Data
Aug. 31, 2012    (JP) ................. 2012-191080

(51) Int. Cl.
| C07D 277/56 | (2006.01) |
| A61K 47/40 | (2006.01) |
| C07D 277/20 | (2006.01) |
| C07D 211/22 | (2006.01) |
| A61K 31/426 | (2006.01) |
| C08B 37/16 | (2006.01) |
| C08L 5/16 | (2006.01) |

(52) U.S. Cl.
CPC .......... *C07D 277/56* (2013.01); *A61K 31/426* (2013.01); *A61K 47/40* (2013.01); *C07D 211/22* (2013.01); *C07D 277/20* (2013.01); *C08B 37/0015* (2013.01); *C08L 5/16* (2013.01); *C07B 2200/13* (2013.01)

(58) Field of Classification Search
CPC .................................................... C07D 277/56
See application file for complete search history.

(56) References Cited

U.S. PATENT DOCUMENTS

| 6,288,119 | B1 | 9/2001 | Ohuchida et al. |
| 7,402,605 | B2 | 7/2008 | Tani et al. |
| 8,410,281 | B2 | 4/2013 | Ohmoto et al. |
| 2005/0020686 | A1 | 1/2005 | Maruyama et al. |
| 2005/0124577 | A1 | 6/2005 | Tani et al. |
| 2006/0109102 | A1 | 5/2006 | Gortz et al. |
| 2007/0129327 | A1 | 6/2007 | Ohmoto et al. |
| 2008/0021021 | A1 | 1/2008 | Okada et al. |
| 2009/0227644 | A1 | 9/2009 | Ohmoto et al. |
| 2012/0088805 | A1 | 4/2012 | Ohmoto et al. |

FOREIGN PATENT DOCUMENTS

| CN | 101237885 A | 8/2008 |
| EP | 0 156 611 A2 | 10/1985 |
| EP | 1 481 976 A1 | 12/2004 |
| EP | 1 586 564 A1 | 10/2005 |
| EP | 1 609 480 A1 | 12/2005 |
| EP | 1 707 208 A1 | 10/2006 |
| EP | 1 782 830 A1 | 5/2007 |
| EP | 1 806 148 A1 | 7/2007 |
| EP | 1 886 693 A1 | 2/2008 |
| FR | 2204408 A | 5/1974 |
| JP | 11-130678 A | 5/1999 |
| WO | 03/009872 A1 | 2/2003 |
| WO | 03/074483 A1 | 9/2003 |
| WO | 2004/065365 A1 | 8/2004 |
| WO | 2004/089411 A1 | 10/2004 |
| WO | 2005/053707 A1 | 6/2005 |
| WO | 2005/061492 A1 | 7/2005 |
| WO | 2006/016689 A1 | 2/2006 |
| WO | 2006/043655 A1 | 4/2006 |
| WO | 2006/129788 A1 | 12/2006 |
| WO | 2009/148163 A1 | 12/2009 |
| WO | 2010/143661 A1 | 11/2013 |

OTHER PUBLICATIONS

State Intellectual Property Office of the People's Republic of China, Communication dated Oct. 19, 2015, issued in counterpart Chinese Patent Application No. 201380045485.X.
New Zealand Patent Office, Communication dated Jul. 1, 2010, issued in N.Z. Patent Application No. 563863.
European Patent Office, Communication dated Jun. 10, 2010, issued in EP Patent Application No. 06756919.4.
Russian Patent Office, Communication dated Jun. 23, 2010, issued in Russian Patent Application No. 2007148992/15.
Chinese Patent Office, Communication dated Jun. 9, 2010, issued in CN Patent Application No. 200680028685.4.
European Patent Office, Communication dated Feb. 12, 2010, issued in EP Patent Application No. 04819909.5.
Hiroyuki Kato et al., "Successful Treatment of Intermittent Claudication Due to Spinal Canal Stenosis Using Beraprost Sodium, a Stable Prostaglanding I2 Analogue", The Journal of Vascular Diseases, vol. 48, No. 5, May 1997, pp. 457-461.
K. Yone et al., "The effest of Lipo prostaglandin E1 on cauda equina blood flow in patients with lumbar spinal canal stenosis: myeloscopic observation", Spinal Cord, 1999, 6 pgs. total.

(Continued)

*Primary Examiner* — Laura L. Stockton
(74) *Attorney, Agent, or Firm* — Sughrue Mion, PLLC

(57) ABSTRACT

A compound that can be a therapeutic agent for underactive bladder which has low risk of side effects and can be administered orally is provided. Furthermore, a crystal which is advantageous in view of the stability, long-term storage, handleability, easiness of the drug preparation or the like as a drug substance of medicaments is provided. Since a salt of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid or a diastereomeric mixture thereof and 4-piperidinemethanol is a chemically very stable crystal, it can be stored for a long time, and is very useful as a drug substance of medicaments.

28 Claims, 6 Drawing Sheets

(56) References Cited

OTHER PUBLICATIONS

Shinichi Konno, et al., "Effects of OP-1206 (Prostaglandin E1 ), on Nerve-Conduction Velocity in the Dog Cauda Equina Subjected to Acute Experimental Compression", Journal of Spinal Disorders, vol. 9, No. 2, 1996, pp. 103-106.
Judita Orendacova et al., "Cauda equina syndrome", Progress in Neurobiology, 2001, pp. 613-637, XP002565081.
European Patent Office, Communication dated Feb. 2, 2010, issued in EP Patent Application No. 06756919.4.
Israeli Patent Office, Communication dated Mar. 10, 2010, issued in Israeli Patent Application No. 187840.
Y. Liu, et al., "Comparison the Effect of Beraprost Sodium with that of Limaprost Alfadex in rat Neuropathic Intermittent Claudication Model", vol. 30, No. 10, 2002, 3 pgs. total.
Michitaka Kiriyama, et al., "Ligand binding specificities of the eight types and subtypes of the mouse prostanoid receptors expressed in Chinese hamster ovary", British Journal of Pharmacology, 1997, pp. 217-224.
H. Kuwada "Effects of prostaglandin derivatives on changes of gastric mucosal protein contents in ethanol-induced ulcer", Cytoprotection & Biology, 1985, pp. 217-225.
Kiyohiro Tsutsui "Procyclin Naifuku Toya go Soki Shita Livedo kekkan'en No. 1 Rei", The Journal of Medicine, 1994, pp. 611-613.
International Searching Authority, Communication dated Feb. 1, 2005, issued in Int. Patent Application No. PCT/JP2004/017961.
Masako Bilak et al., "PGE2 Receptors Rescue Motor nerons in a Model of Amyotrophic Lateral Sclerosis", Annals of Neurology, vol. 56, No. 2, Aug. 2004, pp. 240-248.
U.S. Patent Office, Communication dated Feb. 22, 2010, issued in U.S. Appl. No. 11/916,374.
U.S. Patent Office, Communication dated Aug. 30, 2010, issued in U.S. Appl. No. 11/916,374.
U.S. Patent Office, Communication dated Sep. 17, 2012, issued in U.S. Appl. No. 12/889,731.
Jun Han "Advances in Characterization of Pharmaceutical Hydrates", Trends in Pharmaceutical Industry, Mar. 2006, 6 pgs. total.
Velentino J. Stella, et al. "Prodrugs: Challenges and Rewards", Part 1, Biotechnology: Pharmaceutical Aspect, 2007, 17 pgs. total.
Sudha R. Vippagunta et al., "Crystalline solids", Advanced Drug Delivery Reviews, Dec. 21, 2001, pp. 3-26.
U.S. Patent Office, Communication dated Sep. 7, 2011, issued in U.S. Appl. No. 12/944,326.
U.S. Patent Office, Communication dated Oct. 11, 2011, issued in U.S. Appl. No. 12/944,326.
U.S. Patent Office, Communication dated Jun. 21, 2012, issued in U.S. Appl. No. 12/944,326.
U.S. Patent Office, Communication dated Oct. 30, 2012, issued in U.S. Appl. No. 12/944,326.
U.S. Patent Office, Communication dated Apr. 12, 2013, issued in U.S. Appl. No. 13/750,076.
U.S. Patent Office, Communication dated Aug. 26, 2013, issued in U.S. Appl. No. 13/750,076.
A.D. Desmond, et al., "Clinical Experience with Intravesical Prostaglanding E2", British Journal of Urology, 1980, pp. 357-366.
Karl-Erik Andersson "Pharmacology of the Lower Urinary Tract: Basis for Current and Future Treatments of Urinary Incontinence", Pharmacological Reviews, Vo. 56, No. 4, 2004, pp. 581-631, XP002684367.
European Patent Office, Communication dated Nov. 2, 2012, issued in EP Patent Application No. 10786192.4.
European Patent Office, Communication dated Nov. 15, 2012, issued in EP Patent Application No. 10786192.4.
Japanese Patent Office, Communication dated Mar. 29, 2011, issued in JP Patent Application No. 2011-503274.
U.S. Patent Office, Communication dated Jun. 15, 2012, issued in U.S. Appl. No. 13/377,047.
U.S. Patent Office, Communication dated Dec. 7, 2012, issued in U.S. Appl. No. 13/377,047.
Russian Patent Office, Communication dated Feb. 27, 2014, issued in RU Patent Application No. 2011152927/04.
"Chemical Encyclopedic Dictionary", Moscow, Sovetskaya Entsiclopediya, 1983, pp. 130-131.
MiD. Mashkovsky "Lekarstvennye sredstva (Drugs) Manual for physicians", Moscow, OOO "Novaya volna", vol. 1, 2001, pp. 6-7.
Chinese Patent Office, Communication dated Feb. 20, 2014, issued in CN Patent Application No. 201080035423.7.
Msayuki Takeda, et al., "The Forefront for Novel Therapeutic Agents Based on the Pathophysiology of Lower Urinary tract Dysfunction: Pathophysiology of Voiding Dysfunction and Pharmacological Therapy", Journal of Pharmacological Sciences, 2010, pp. 121-127.
U.S. Patent Office, Communication dated Jun. 20, 2013, issued in U.S. Appl. No. 13/784,008.
U.S. Patent Office, Communication dated Nov. 13, 2013, issued in U.S. Appl. No. 13/784,008.
U.S. Patent Office, Communication dated Apr. 4, 2014, issued in U.S. Appl. No. 13/784,008.
U.S. Patent Office, Communication dated Aug. 13, 2014, issued in U.S. Appl. No. 14/178,901.
U.S. Patent Office, Communication dated Jan. 2, 2015, issued in U.S. Appl. No. 14/178,901.
International Searching Authority, Communication dated Aug. 22, 2006, issued in Int. Patent Application No. PCT/JP2006/311084.
International Searching Authority, Communication dated Aug. 24, 2010, issued in Int. Patent Application No. PCT/JP2010/059771.
Int. Search Report dated Nov. 5, 2013 issued in Int. Application No. PCT/JP2013/073442 (PCT/ISA/210).
State Intellectual Property Office of the People's Republic of China, communication dated Jul. 5, 2016, issued in corresponding Chinese Application No. 201380045485.X.
Vietnamese Intellectual Property Office, Communication dated Jul. 28 2016 issued in corresponding Vietnamese Application No. 1-2015-00680.
Communication dated Aug. 9, 2016, issued by the Mexican Patent Office in corresponding Mexican application No. MX/a/2015/002209.
Japanese Patent Office, Office Action drafted Jan. 27, 2017, issued in corresponding Japanese Patent Application No. 2014-533137.
State Intellectual Property Office of P.R. China, Office Action dated Mar. 7, 2017, issued in a corresponding Chinese Application No. 201380045485.X.

AMINE SALT AND CRYSTALS THEREOF

TECHNICAL FIELD

The present invention relates to: a salt of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid or a diastereomeric mixture thereof and 4-piperidinemethanol; a crystal thereof; or a cyclodextrin clathrate thereof (hereinafter, sometimes referred to as the compound of the present invention): and relates to a pharmaceutical composition containing the same.

With regard to a symptom wherein bladder cannot be empty (incomplete bladder emptying) resulting from insufficient micturition contraction, a new terminology of underactive bladder has recently been proposed.

Underactive bladder is caused by bladder contraction dysfunction, i.e. a clinical condition wherein contractility of the bladder detrusor is decreased (detrusor underactivity), or a combination of urethral relaxation dysfunction (lower urinary tract passage dysfunction), i.e. a clinical condition with insufficient relaxation of the urethral sphincter and bladder contraction dysfunction, which is classified into neurogenic underactive bladder, myogenic underactive bladder, drug-induced underactive bladder, age-related underactive bladder, and underactive bladder induced by other factors (e.g., underactive bladder due to lower urinary tract obstruction, infection and stress etc.) depending on the causes.

As a compound capable of treating underactive bladder, 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid, which has an effect of contracting bladder detrusor and relaxing urethral sphincter, is known (see Patent Literature 1).

However, so far, no document has disclosed the salt of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid and 4-piperidinemethanol, the crystals thereof and the polymorphism.

CITATION LIST

Patent Literature

[Patent Literature 1] WO2010/143661

SUMMARY OF INVENTION

Problem to be Solved by Invention

2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid has a strong effect of contracting bladder detrusor and relaxing urethral sphincter and is very useful as a therapeutic agent for underactive bladder. However, 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid is an amorphous oily substance, and thus it is very difficult to handle and is unstable as a drug substance during the preparation of a drug substance for producing an oral preparation.

Since chronic diseases such as underactive bladder require long-term administration of a drug, a therapeutic agent which has, needless to say, a strong effect, has low risk of side effects and can be administered orally has been desired when the safety and convenience of patients are taken into consideration.

When an oral preparation for long-term administration is produced, in particular, the drug substance thereof should be stable against heat, humidity or the like and should be safe. When a drug substance can be obtained in a stable form such as a crystal form, it is highly advantageous in view of the stability, long-term storage, handleability, easiness of the drug preparation or the like. Accordingly, acquisition of a crystal of a drug substance which is chemically stable and safe is a critical problem for the production of medicaments.

Means for Solving Problem

The inventors of the present invention attempted to crystallize salts of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid and 25 safe bases which have been approved as medicaments, including salts with alkali metals (potassium, sodium and the like), salts with alkaline-earth metals (calcium, magnesium and the like) and salts with pharmaceutically acceptable organic amines such as triethylamine, diethanolamine, dicyclohexylamine, lysine and arginine. However, none of the salts could be crystallized. The inventors of the present invention further examined a huge number of bases of about 100 kinds under various conditions for crystallization, and as a result found that the salt of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid and 4-piperidinemethanol can be a chemically stable and safe crystal. The present invention was thus accomplished.

Namely, the present invention relates to:

1. a salt of a compound represented by formula (I)

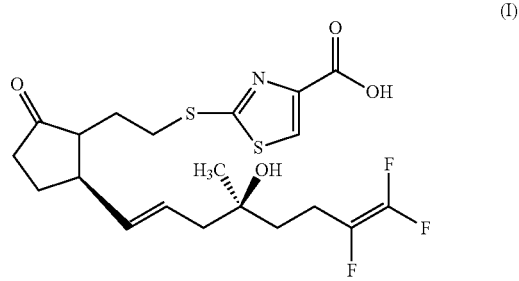 [SMILES: C[C@@](O)(C/C=C/[C@H]1CCC(=O)C1CCSc1nc(C(=O)O)cs1)CCC(F)=C(F)F]

(wherein

⟆ represents an α-configuration,

⟋ represents a β-configuration, and

⟋ represents an α-configuration, a β-configuration or a mixture thereof in an arbitrary ratio) or a diastereomeric mixture thereof and 4-piperidinemethanol; a crystal thereof; or a cyclodextrin clathrate thereof;

2. the salt, the crystal thereof or the cyclodextrin clathrate thereof described in 1 above, wherein the compound represented by formula (I) is 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid;

3. the salt, the crystal thereof or the cyclodextrin clathrate thereof described in 1 above, wherein the compound represented by formula (I) is a diastereomeric mixture of 2-[(2-

{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid;

4. the salt, the crystal thereof or the cyclodextrin clathrate thereof described in 3 above, wherein the diastereomer of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid is 2-[(2-{(1S,5R)-2-oxo-5-[(1E,4S)-7,8,8-trifluoro-4-hydroxy-4-methyl-1,7-octadien-1-yl]cyclopentyl}ethyl)thiol]-1,3-thiazole-4-carboxylic acid;

5. piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a diastereomeric mixture thereof, a crystal thereof or a cyclodextrin clathrate thereof;

6. piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a crystal thereof or a cyclodextrin clathrate thereof;

7. a mixture of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate and a diastereomer thereof: piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a crystal thereof, or a cyclodextrin clathrate thereof;

8. a compound represented by formula (II)

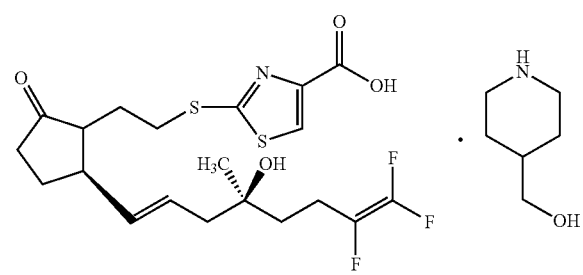

(II)

(wherein $\overset{\text{\tiny{,,,,,}}}{\rule{1em}{0.4pt}}$ represents an α-configuration, $\overset{}{\rule{1em}{0.4pt}}$ represents a β-configuration, and $\overset{}{\rule{1em}{0.4pt}}$ represents an α-configuration, a β-configuration or a mixture thereof in an arbitrary ratio), a crystal thereof or a cyclodextrin clathrate thereof;

9. the crystal or the cyclodextrin clathrate thereof described in any one of 1 to 8 above which has a crystalline form having 2θ peaks at least at approximately 9.05, 9.44, 12.61, 13.96 and 18.09° in a powder X-ray diffraction spectrum;

10. the crystal or the cyclodextrin clathrate thereof described in 9 above which has a crystalline form having 2θ peaks at least at approximately 9.05, 9.44, 12.61, 13.96, 18.09, 18.91, 19.42, 20.53, 21.77, 22.60, 23.38 and 24.59° in a powder X-ray diffraction spectrum;

11. the crystal or the cyclodextrin clathrate thereof described in any one of 1 to 8 above which has a crystalline form having a substantially same powder X-ray diffraction spectrum as the powder X-ray diffraction spectrum shown in FIG. 1;

12. the crystal or the cyclodextrin clathrate thereof described in any one of 9 to 11 above which has a crystalline form having an onset of an endothermic peak at approximately 118° C. in differential scanning calorimetry;

13. the crystal or the cyclodextrin clathrate thereof described in any one of 9 to 11 above which has a crystalline form having the chart of differential scanning calorimetry shown in FIG. 2;

14. the crystal or the cyclodextrin clathrate thereof described in any one of 1 to 8 above which has a crystalline form having 2θ peaks at least at approximately 8.91, 9.71, 11.97, 13.23 and 15.88° in a powder X-ray diffraction spectrum;

15. the crystal or the cyclodextrin clathrate thereof described in 14 above which has a crystalline form having 2θ peaks at least at approximately 8.91, 9.71, 11.97, 13.23, 15.88, 18.63, 19.02, 21.02, 22.91 and 23.85° in a powder X-ray diffraction spectrum;

16. the crystal or the cyclodextrin clathrate thereof described in any one of 1 to 8 above which has a crystalline form having a substantially same powder X-ray diffraction spectrum as the powder X-ray diffraction spectrum shown in FIG. 3;

17. the crystal or the cyclodextrin clathrate thereof described in any one of 14 to 16 above which has a crystalline form having an onset of an endothermic peak at approximately 113° C. in differential scanning calorimetry;

18. the crystal or the cyclodextrin clathrate thereof described in any one of 14 to 16 above which has a crystalline form having the chart of differential scanning calorimetry shown in FIG. 4;

19. the crystal or the cyclodextrin clathrate thereof described in any one of 1 to 8 above which has a crystalline form having 2θ peaks at least at approximately 9.11, 13.43, 16.16, 17.77 and 18.69° in a powder X-ray diffraction spectrum;

20. the crystal or the cyclodextrin clathrate thereof described in 19 above which has a crystalline form having 2θ peaks at least at approximately 9.11, 13.43, 16.16, 17.77, 18.69, 19.24, 19.86, 21.19, 22.72 and 24.20° in a powder X-ray diffraction spectrum;

21. the crystal or the cyclodextrin clathrate thereof described in any one of 1 to 8 above which has a crystalline form having a substantially same powder X-ray diffraction spectrum as the powder X-ray diffraction spectrum shown in FIG. 5;

22. the crystal or the cyclodextrin clathrate thereof described in any one of 19 to 21 above which has a crystalline form having an onset of an endothermic peak at approximately 118° C. in differential scanning calorimetry;

23. the crystal or the cyclodextrin clathrate thereof described in any one of 19 to 21 above which has a crystalline form having the chart of differential scanning calorimetry shown in FIG. 6;

24. a pharmaceutical composition containing as an active ingredient: a salt of a compound represented by formula (I)

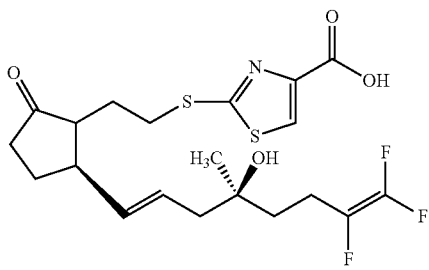

(wherein

..ıllı represents an α-configuration,

◂ represents a β-configuration, and

◂ represents an α-configuration, a β-configuration or a mixture thereof in an arbitrary ratio) or a diastereomeric mixture thereof and 4-piperidinemethanol; a crystal thereof; or a cyclodextrin clathrate thereof;

25. a pharmaceutical composition containing the crystal or the cyclodextrin clathrate thereof described in any one of 9 to 23 above;

26. the pharmaceutical composition described in 24 or 25 above which is an agent for contracting bladder detrusor and relaxing urethral sphincter;

27. the pharmaceutical composition described in 26 above which is an agent for preventing, treating and/or ameliorating bladder contraction dysfunction and/or urethral relaxation dysfunction; and 28. the pharmaceutical composition described in 27 above, wherein the bladder contraction dysfunction and/or the urethral relaxation dysfunction are underactive bladder.

Effects of Invention

Since the compound of the present invention is a chemically very stable crystal, the compound can be stored for a long time and is very useful as a drug substance of medicaments.

In addition, because the compound of the present invention has an effect of contracting bladder detrusor and relaxing urethral sphincter, the compound ameliorates bladder contraction dysfunction and/or urethral relaxation dysfunction and is effective as an agent for preventing and/or treating underactive bladder. Furthermore, the compound is effective also as an agent for ameliorating various symptoms of underactive bladder. Thus, when the compound of the present invention, which is a stable crystal, is used as a drug substance and an oral preparation for long-term administration is produced, the preparation can be a highly effective therapeutic agent for underactive bladder.

DESCRIPTION OF EMBODIMENTS

Figure 1:
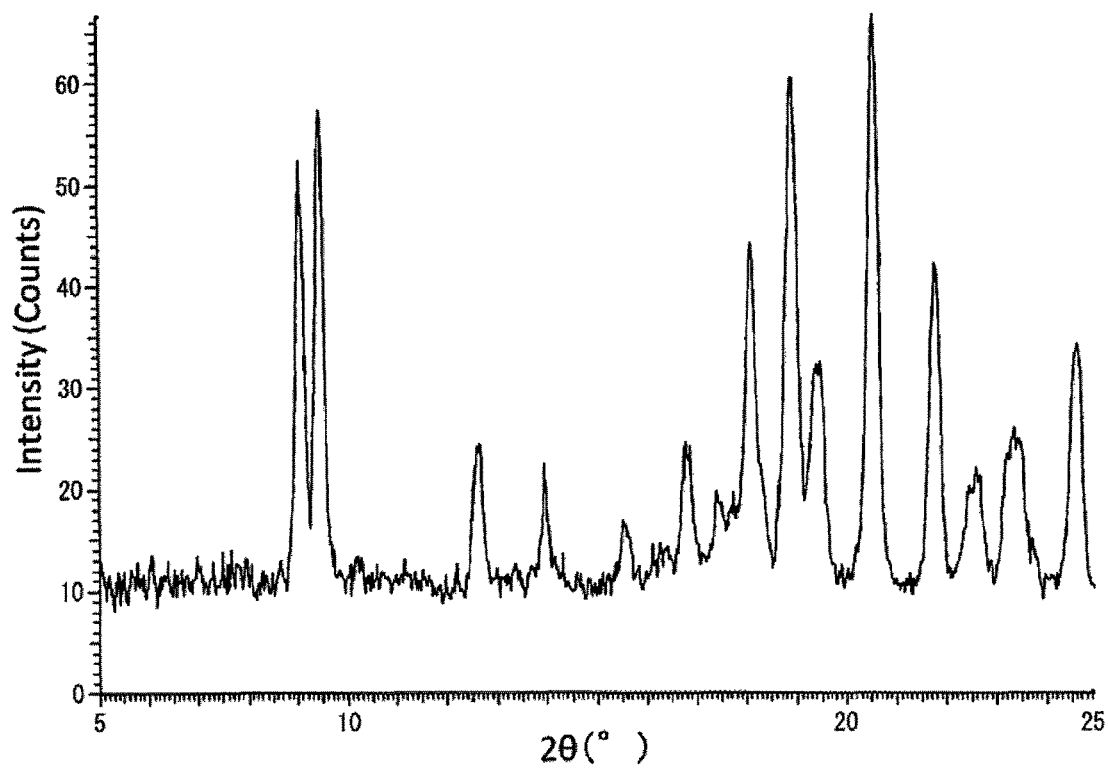
FIG. 1 shows the powder X-ray diffraction spectrum of Crystalline form A of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (hereinafter, sometimes abbreviated to Compound 18). The term "Intensity" in the figure means the diffraction intensity.

The present invention relates to (1) the salt of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (hereinafter, sometimes abbreviated to Compound 17) and 4-piperidinemethanol, (2) a salt of a diastereomer of Compound 17 and 4-piperidinemethanol, (3) a salt of a diastereomeric mixture of Compound 17 in an arbitrary ratio and 4-piperidinemethanol, (4) crystals of (1) to (3) above, (5) cyclodextrin clathrates of (1) to (4) above, and (6) pharmaceutical compositions containing (1) to (5) above.

Compound 17 is a compound represented by the following formula

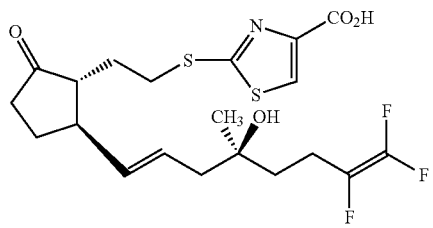 [SMILES: C[C@@](O)(C/C=C/[C@H]1CCC(=O)[C@@H]1CCSc1nc(C(=O)O)cs1)CCC(F)=C(F)F]

and described in Example 17 of WO2010/143661.

Unless otherwise specifically indicated herein, it is apparent to those skilled in the art that the symbol ..ıllı represents a binding to the far side of the paper (i.e. α-configuration);

the symbol ◂ represents a binding to the front of the paper (i.e. β-configuration); and the symbol ◂ represents α-configuration, β-configuration or a mixture thereof.

Various salts of Compound 17 were prepared and examined for crystallization by the following method.

Namely, Compound 17 (10 mg) was dissolved in methanol (200 μL) and various bases were added thereto. Then, the mixture was concentrated under reduced pressure and trituration was conducted with using various solvents. For the examination, ethyl acetate, methyl t-butyl ether, n-hexane and the like were used as the solvents.

Although examination for crystallization was conducted with using 100 salts or more, crystalline solids could not be obtained except for the salt with 4-piperidinemethanol. For example, salts with alkali metals (potassium, sodium and the like) and salts with alkaline-earth metals (calcium, magnesium and the like), which have been approved as medicaments, and salts of Compound 17 with pharmaceutically acceptable organic amines such as triethylamine, diethanolamine, dicyclohexylamine, lysine and arginine, and with 4-piperidineethanol, 4-methylpiperidine and 4-hydroxypiperidine, which have very similar structures to that of 4-piperidinemethanol, were amorphous oily substances.

Some of the results are shown below.

TABLE 1

| Counter base | State |
|---|---|
| Sodium | Oily |
| Potassium | Oily |
| Calcium | Oily |
| Magnesium | Oily |
| Triethylamine | Oily |
| Diethanolamine | Oily |
| Dicyclohexyl amine | Oily |
| t-Butylamine | Oily |
| Lysine | Oily |
| Arginine | Oily |
|  | Oily |
|  | Oily |
|  | Oily |
|  | Oily |
|  | Oily |
|  | Oily |
|  | Oily |
|  | Oily |
| (isoindoline) | Oily |
| (diallylamine) | Oily |
| (azepane) | Oily |
| (tetrahydropyridine) | Oily |

TABLE 1-continued

| Counter base | State |
|---|---|
| (2-methylimidazole) | Oily |
| (prolinol) | Oily |
| (1-methylpiperidine) | Oily |
| (4-methoxypiperidine) | Oily |
| (4-piperidinemethanol) | Crystalline solid |
| (4-piperidineethanol) | Oily |
| (4-methylpiperidine) | Oily |
| (4-hydroxypiperidine) | Oily |

Furthermore, the polymorphism of the salt of Compound 17 and 4-piperidinemethanol was examined. The polymorphism was confirmed by powder X-ray diffraction analysis, differential scanning calorimetry and thermogravimetry. The powder X-ray diffraction analysis, differential scanning calorimetry and thermogravimetry can be measured for example under the conditions described in the Examples below.

As a result of extensive research by the inventors of the present invention, it was demonstrated that there are more than one polymorphism for Compound 18, which is the salt of Compound 17 and 4-piperidinemethanol. Although all the crystals are stable and preferable, Crystalline form C (the crystalline form obtained in Example 18(3) in the present specification) is preferable among them.

The compound of the present invention can be converted to a cyclodextrin clathrate using α-, β- or γ-cyclodextrin or a mixture thereof by any the methods described in the specifications of Japanese Patent Publication Nos. JP-B-S50-3362, JP-B-S52-31404 and JP-B-S61-52146. By converting into the cyclodextrin clathrate, since stability is increased and solubility in water is increased, the compound is convenient in case of use as a drug. The inclusion of the compound of the present invention in cyclodextrin can be determined by differential scanning calorimetry or powder X-ray diffraction analysis.

There are diastereomers for Compound 17 and Compound 18. Thus, the present invention also includes a salt of a diastereomer of Compound 17 and 4-piperidinemethanol, a salt of a diastereomeric mixture of Compound 17 in an arbitrary ratio and 4-piperidinemethanol, diastereomers of Compound 18 and a diastereomeric mixture of Compound 18 in an arbitrary ratio.

There are seven possible diastereomers for Compound 17. An example of the diastereomers of Compound 17 is the following compound, which can exist with Compound 17 at equilibrium:

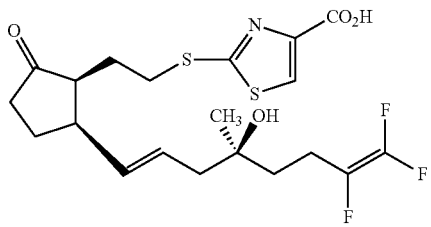 [SMILES: C[C@@](O)(C/C=C/[C@H]1CCC(=O)[C@H]1CCSc1nc(C(=O)O)cs1)CCC(F)=C(F)F]

2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (the compound described in Example 20 of WO2010/143661). The diastereomeric mixture of Compound 17 means a mixture of any two or more kinds selected from Compound 17 and the seven diastereomers thereof. In the present invention, as the diastereomeric mixture of Compound 17, all the diastereomeric mixtures containing Compound 17 are preferable. However, a diastereomeric mixture containing Compound 17 and 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid is more preferable, and a mixture of Compound 17 and 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid is particularly preferable.

Compound 17, 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid or a mixture thereof is sometimes represented by formula (I) below.

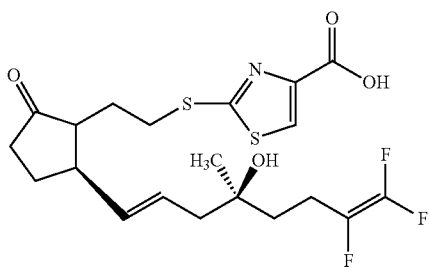

(In the formula

⬙⬙⬙ represents an α-configuration,

➚ represents a β-configuration, and

╱ represents an α-configuration, a β-configuration or a mixture thereof in an arbitrary ratio.)

There are seven possible diastereomers for Compound 18. An example of the diastereomers of Compound 18 is piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, which can exist with Compound 18 at equilibrium. The diastereomeric mixture of Compound 18 means a mixture of any two or more kinds selected from Compound 18 and the seven diastereomers thereof. In the present invention, as the diastereomeric mixture of Compound 18, all the diastereomeric mixtures containing Compound 18 are preferable. However, a diastereomeric mixture containing Compound 18 and piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate is more preferable, and a mixture of Compound 18 and piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate is particularly preferable.

Compound 18, piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate or a mixture thereof is sometimes represented by formula (II) below.

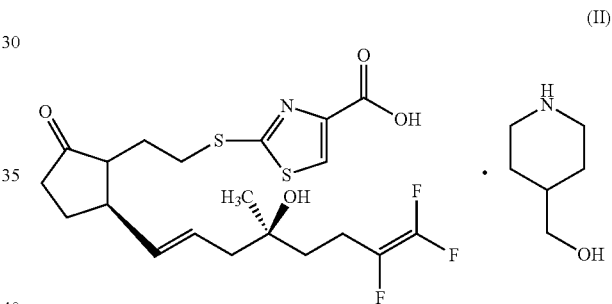

(In the formula,

⬙⬙⬙ represents an α-configuration,

➚ represents α-configuration, and

╱ represents an α-configuration, a β-configuration or a mixture thereof in an arbitrary ratio.)

In addition, the compound represented by formula (II) is sometimes described as piperidin-4-ylmethanol 2-[(2-{1-ambo-(5R)-2-oxo-5-[(1E,4S)-7,8,8-trifluoro-4-hydroxy-4-methylocta-1,7-dien-1-yl]cyclopentyl}ethyl)sulfanyl]-1,3-thiazole-4-carboxylate.

Here, although the diastereomeric excess percentage of Compound 17 or Compound 18 is not particularly limited, the percentage is preferably from 60 to 100% d.e., further preferably from 60 to 99.9% d.e. and particularly preferably from 80 to 99% d.e.

In addition, the diastereomeric mixture of Compound 17 or Compound 18 in an arbitrary ratio is preferably a mixture in which the percentage of Compound 17 or Compound 18 is 80% or more and 99.9% or less of the whole mixture and further preferably a mixture in which the percentage of Compound 17 or Compound 18 is 90% or more and 99% or less of the whole mixture.

Furthermore, a mixture in which the ratio of Compound 17:diastereomer is about 9:1 is preferable. Also, a mixture in which the ratio of Compound 18:diastereomer is about 9:1 is preferable.

The salt of the diastereomeric mixture of Compound 17 and 4-piperidinemethanol may form a crystal. Moreover, Compound 18 may form a crystal with the diastereomers thereof.

[Preparation Methods of the Compound of the Present Invention]

The compounds of the present invention can be prepared by appropriately modifying and combining methods known in the art, for example, methods described in the pamphlets of International Publication No. WO 2010/143661, Synlett 2002, No. 1, 239-242 or Comprehensive Organic Transformations: A Guide to Functional Group Preparations, 2nd Edition (Richard C. Larock, John Wiley & Sons Inc, 1999), methods shown below or methods shown in Examples.

[Toxicity]

The compound of the present invention causes less side effects and is thus safe enough to use as a drug.

[Applications to Medicaments]

Since the compound of the present invention acts on smooth muscles, particularly the bladder detrusor and the urethral sphincter, to promote the contraction of the bladder detrusor and the relaxation of the urethral, sphincter, it can ameliorate bladder contraction dysfunction and urethral relaxation dysfunction and is thus effective as an agent for preventing and/or treating underactive bladder. Additionally, the compound of the present invention is effective as an agent for ameliorating various symptoms associated with underactive bladder, for example, slow urine stream, split urine stream, blocked urine stream, delayed urination, abdominal pressure voiding, feeling of residual urine, overflow incontinence, anuresis and/or drop of urine after urination. The compound of the present invention is particularly effective as an agent for ameliorating split urine stream, blocked urine stream, abdominal pressure voiding, feeling of residual urine, overflow incontinence, anuresis and/or drop of urine after urination.

The compound of the present invention is also effective in preventing and/or treating spinal canal stenosis, cervical spondylosis, diseases of the peripheral nervous system, immune diseases (amyotrophic lateral sclerosis (ALS), multiple sclerosis, Sjogren's syndrome, chronic articular rheumatism, autoimmune diseases such as systemic erythematodes, rejection responses after organ transplantation, etc.), allergic diseases (for example, bronchial asthma, allergic nasal inflammation, allergic conjunctiva inflammation, atopic dermatitis, food allergy etc.), nerve cell death, dysmenorrhea, premature birth, misbirth, calvities, neural retinal diseases such as glaucoma, erectile dysfunction, arthritis, lung injury, fibroid lung, emphysema, bronchitis, chronic obstructive respiratory diseases, liver injury, acute hepatitis, cirrhosis, shock, nephritis (for example, acute nephritis, chronic nephritis etc.), renal dysfunction, pancreatitis, systemic inflammatory response syndrome, sepsis, hemophagocytic syndrome, macrophage activation syndrome, Still's disease, Kawasaki disease, burn injury, systemic granulomatous diseases, colitis ulcerosa, Crohn's disease, hypercytokinemia on dialysis, multiple organ dysfunction, bone diseases (bone fracture, refracture, intractable fracture, bone adhesion dysfunction, false joint, osteohalisteresis, bone Paget's disease, rigid spondylitis, cancer bone metastasis, arthrosis deformans, bone cartilage breakdown in similar diseases thereof etc.).

The compound of the present invention, it may be administered in combination with other drugs as a combined agent for the purpose of 1) supplementing and/or enhancing the prophylactic and/or therapeutic effects of the compound, 2) improving the pharmacokinetics and absorption of the compound, reducing the dose of the compound, and/or 3) alleviating the side effects of the compound.

With regard to the combination agent of the compound of the present invention and other drugs, it may be administered in combination with other drugs in the form of a blend in which the two ingredients are mixed in one preparation or in separate preparations. The administration of the two ingredients in separate preparations includes simultaneous administration and administration with a time interval. In administration with a time interval, it is possible that the compound of the present invention is administered in advance and the other drugs are administered later or it is possible that the other drugs are administered in advance and the compound of the present invention is administered later, wherein the administration modes of the two ingredients may be the same as or different from each other.

Examples of drugs suitable for supplementing and/or enhancing the effects of the compound of the present invention include acetylcholinesterase inhibitors (for example, distigmine and neostigmine etc.) and al acceptor antagonists (for example, tamsulosin, prazosin, alfuzosin, naftopidil, urapidil etc.).

There is no particular limitation on the weight ratio of the compound of the present invention to the other drugs.

The other drugs may be a combination of drugs of the same kind or two or more different kinds.

The other drug for supplementing and/or enhancing the effects of the compound of the present invention include not only currently found drugs and drugs which will be found based on the above mechanism.

In case where a combination agent of the compound of the present invention with the other drugs is used for the above purposes, it is usually administered systemically or locally, or orally or parenterally.

Although the dose may vary depending on the kind of the drug and may depend on age, weight, symptoms, intended therapeutic effects, administration methods, treatment time etc., the compound of the present invention may be usually administered orally at a dose ranging from 1 ng to 100 mg each time per an adult once or several times per day or, may be administered parenterally at a dose ranging from 0.1 ng to 10 mg each time per an adult once or several times per day or alternatively, may be continuously administered intravenously over a period of 1 to 24 hr per day.

Since the dose may vary depending on various conditions as described above, there is a case wherein the dose is sufficient with smaller amount than the dose described above while there is a case wherein administration with larger scope than the scope described above is necessary.

In case where the compound of the present invention or the combination agent of the compound of the present invention and other drug is administered, it may be used as internal solid preparations or internal liquid preparations for oral administration and injectables, external preparations, suppository and inhalations etc. for parenteral administration.

Examples of internal solid preparations suitable for oral administration includes tablets, pills, capsules, powders and granules. The capsules include hard capsules and soft capsules.

The internal solid preparations may be prepared using only one or more active ingredients or by mixing one or more active ingredients with for example, an excipient (lactose, mannitol, glucose, microcrystalline cellulose, starch etc.), a binder (hydroxypropyl cellulose, polyvinylpyrrolidone, alumina magnesium metasilicate etc.), a disintegrant (calcium carboxymethyl cellulose etc.), a lubricant (magnesium stearate etc.), a stabilizer or a dissolution aid (glutamic acid, asparaginic acid etc.) with formulation by techniques known in the art. If necessary, the solid preparations may be covered with a coating agent (for example, white sugar, gelatin, hydroxypropyl cellulose, hydroxypropyl methyl cellulose phthalate etc.) and may be covered with two or more layers. Capsules of absorbable materials, for example, gelatin, are also included.

Examples of internal liquid preparations suitable for oral administration include pharmaceutically acceptable aqueous solutions, suspending agents, emulsifying agents, syrups elixirs etc. In such a liquid preparation, one or more active substances are dissolved, suspended or emulsified in a diluent which is generally used in the art (for example, distilled water, ethanol, a mixed solution thereof etc.). The liquid preparations may contain a wetting agent, a suspending agent, an emulsifying agent, a sweetening agent, a flavoring agent, an aromatic agent, a preservative, a buffering agent, etc.

External formulations for parenteral administration include, for example, ointments, gels, creams, poultices, patches, liniments, aerosols, inhalations and sprays. Such a preparation includes one or more active substances and is prepared by methods known or commonly used in the art.

The ointments are prepared by methods known or commonly used in the art. For example, an ointment may be prepared by triturating or melting one or more active substances in a base. The ointment base is selected from those known or commonly used in the art. Examples of such ointment bases include higher fatty acids and higher fatty acid esters (adipic acid, myristic acid, palmitic acid, stearic acid, oleic acid, adipate, myristate, palmitate, stearate, oleate etc.), waxes (beeswax, hard wax, ceresin etc.), surfactants (polyoxyethylene alkyl ether phosphate etc.), higher alcohols (cetanol, stearyl alcohol, cetostearyl alcohol etc.), silicone oil (dimethylpolysiloxane etc.), hydrocarbons (hydrophilic Vaseline, white Vaseline, purified lanolin, liquid paraffin etc.), glycols (ethylene glycol, diethylene glycol, propylene glycol, polyethylene glycol, Macrogols etc.), vegetable oils (castor oil, olive oil, sesame oil, turpentine etc.), animal oils (mink oil, egg oil, squalane, squalene etc.), water, absorption accelerators, and anti-itch agents. These ointment bases may be used alone or as a mixture of two or more thereof. The ointments may further include a moisturizer, a preservative, a stabilizer, an antioxidant, a flavor, etc.

The gels are prepared by methods known or commonly used in the art. For example, a gel may be prepared by melting one or more active substances in a base. The gel base is selected from those known or commonly used in the art. Examples of such gel bases include lower alcohols (ethanol, isopropyl alcohol etc.), gelling agents (carboxymethyl cellulose, hydroxyethyl cellulose, hydroxypropyl cellulose, ethyl cellulose etc.), neutralizing agents (triethanolamine, diisopropanolamine etc.), surfactants (polyethylene glycol monostearate etc.), gums, water, absorption accelerators, and anti-itch agents. These gel bases may be used alone or as a mixture of two or more thereof. The gels may further include a preservative, an antioxidant, a flavor, etc.

The creams are prepared by methods known or commonly used in the art. For example, a cream may be prepared by melting or emulsifying one or more active substances in a base. The cream base is selected from those known or commonly used in the art. Examples of such cream bases include higher fatty acid esters, lower alcohols, hydrocarbons, polyhydric alcohols (propylene glycol, 1,3-butylene glycol, etc.), higher alcohols (2-hexyldecanol, cetanol etc.), emulsifiers (polyoxyethylene alkyl ethers, fatty acid esters etc.), water, absorption accelerators, and anti-itch agents etc.). These cream bases may be used alone or as a mixture of two or more thereof. The creams may further include a preservative, an antioxidant, a flavor, etc.

The poultices are prepared by methods known or commonly used in the art. For example, a poultice may be prepared by melting one or more active substances in a base, kneading, followed by uniformly coating on a support. The poultice base is selected from those known or commonly used in the art. Examples of such poultice bases include thickeners (for example, polyacrylic acid, polyvinylpyrrolidone, arabic gum, starch, gelatin, methyl cellulose etc.), wetting agents (for example, urea, glycerin, propylene glycol etc.), fillers (kaolin, zinc oxide, talc, calcium, magnesium etc.), water, solubilizers, tackifiers, and anti-itch agents. These poultice bases may be used alone or as a mixture of two or more thereof. The poultices may further include a preservative, an antioxidant, a flavor, etc.

The patches are prepared by methods known or commonly used in the art. For example, a patch may be prepared by melting one or more active substances in a base and uniformly coating the melt on a support. The patch base is selected from those known or commonly used in the art. Examples of such patch bases include polymeric bases, oils and fats, higher fatty acids, thickeners, and anti-itch agents. These patch bases may be used alone or as a mixture of two or more thereof. The patches may further include a preservative, an antioxidant, a flavor, etc.

The liniments are prepared by methods known or commonly used in the art. For example, a liniment may be prepared by dissolving, suspending or emulsifying one or more active substances in one or more selected from water, alcohols (ethanol, polyethylene glycol etc.), higher fatty acids, glycerin, soaps, emulsifiers and suspending agents. The liniments may further include a preservative, an antioxidant, a flavor, etc.

The aerosols, inhalations and sprays may contain a stabilizer, such as sodium bisulfite or a buffering agent, for example, an isotonic agent such as sodium chloride, sodium citrate or citric acid which gives isotonicity, in addition to a diluent which is commonly used in the art.

The injectable preparations for parenteral administration may be, for example, solutions, suspensions, emulsions, and solid injectable preparations, which are dissolved or suspended in solvents in use. Such injectable preparation is used by dissolving, suspending or emulsifying one or more active substances in a solvent. Examples of suitable solvents include injectable distilled water, physiological saline, vegetable oils, propylene glycol, polyethylene glycol, alcohols such as ethanol, and combinations thereof. The injectable preparations may include stabilizers, dissolution aids (for example, glutamic acid, asparaginic acid, Polysolvate 80® etc.), suspending agents, emulsifying agents, soothing agents, buffers and preservatives. The injectable preparations are prepared by sterilization or disinfection in final steps. Aseptic solid preparations, for example, lyophilized solid preparations, can also be used by disinfecting or dissolving in aseptic injectable distilled water or other solvents before use.

Examples of the inhalations for parenteral administration include aerosols, powders for inhalation or liquids for inhalation. The liquids for inhalation may be dissolved or suspended in water or other proper medium before use.

The inhalations are prepared by methods known in the art.

For example, a liquid for inhalation is prepared by selecting appropriately preservatives (benzalkonium chloride, paraben etc.), colorants, buffers (sodium phosphate, sodium acetate etc.), isotonic agents (sodium chloride, concentrated glycerin etc.), thickeners (carboxyvinyl polymer etc.) and absorbefacient, depending on the necessity.

A powder for inhalation is prepared by selecting appropriately lubricants (stearic acid, its salts etc.), binders (starch, dextrin etc.), excipients (lactose, cellulose etc.), colorants, preservatives (benzalkonium chloride, paraben etc.) and absorbefacient, depending on the necessity.

For administration of liquids for inhalation, sprayers (atomizers, nebulizers) are usually used. For administration of powders for inhalation, inhalators for the administration of powdery drugs are usually used.

Other compositions for parenteral administration include, one or more active substances and are for example, suppositories for intrarectal administration and pessaries for intravaginal administration.

EXAMPLES

The present invention will be explained in detail by Examples. However, the present invention is not limited by the Examples.

The solvents in the parenthesis indicated in the separated portion by the chromatography and TLC represent eluting or developing solvents used and their ratio is volume ratio.

NMR data are $^1$H-NMR data in 300 MHz unless otherwise specified.

The parentheses in the NMR data represent solvents used for measurement.

In the present specification, powder X-ray measurement, differential scanning calorimetry and thermogravimetry of a crystal were conducted under the following conditions, unless otherwise specifically indicated.

<Measurement Condition for Powder X-Ray>
D8 Discover with GADDS: BRUKER axs
X-ray: Cu/40 kV, 40 mA, Distance to detector: 24.920 cm, Measurement period: 180 seconds, Detector: Hi-STAR detector (two-dimensional PSPC)

<Measurement Condition for Differential Scanning Calorimetry (DSC)>
Temperature range: 25 to 200° C.
Rate of temperature increase: 10° C./min or 5.0° C./min
Gas flow rate: $N_2$, 40 mL/min or Ar, 40 mL/min
Sample pan: aluminum standard 40 µL The compounds used herein were named by a computer program which names chemical names according to the IUPAC rules, ACD/Name Batch (registered trademark), or according to IUPAC nomenclature. For example,

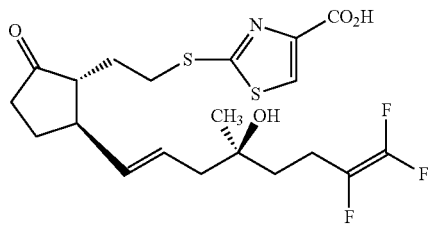 [SMILES: C[C@@](O)(C/C=C/[C@H]1CCC(=O)[C@@H]1CCSc1nc(C(=O)O)cs1)CCC(F)=C(F)F]

was named as 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid.

PREPARATION EXAMPLES

Example 1

4,5,5-trifluoro-N-methoxy-N-methyl-4-penteneamide (Compound 1)

N,O-dimethylhydroxyamine hydrochloride (3.5 g), 1-ethyl-3-(3-dimethylaminopropyl)carbodiimide hydrochloride (6.9 g) and triethylamine (9.2 mL) were added to a solution of 4,5,5-trifluoropent-4-enoic acid (CAS No. 110003-22-0 (5.0 g)) in methylene chloride solution (64 mL) in a cold-water bath and stirring was carried out at room temperature overnight. The reaction solution was concentrated and diluted with ethyl acetate. The dilute solution was washed with 1 N hydrochloric acid, water and saturated brine; dried with anhydrous sodium sulfate; and concentrated to obtain the title compound (6.4 g) having the following physical properties:

TLC: Rf 0.50 (ethyl acetate:hexane=1:2);
NMR (CDCl$_3$): δ 2.51-2.77 (m, 4H), 3.19 (s, 3H), 3.69 (s, 3H).

Example 2

Ethyl 6,7,7-trifluoro-3-oxo-6-heptenoate (Compound 2)

Ethyl acetate (4.8 mL) was slowly added dropwise to a lithium hexamethyldisilazide/tetrahydrofuran solution (1 M, 48 mL) at −78° C., followed by stirring for 30 min. The solution of compound 1 (6.4 g) in anhydrous tetrahydrofuran (33 mL) was slowly added dropwise to the reaction solution at the same temperature followed by stirring for 30 min. To the reaction solution, 2 N hydrochloric acid (30 mL) was added, followed by extraction with ethyl acetate. The organic layer was washed with water and saturated brine; dried with anhydrous sodium sulfate; and concentrated. The resulting residue was purified by silica gel column chromatography (hexane:ethyl acetate=20:1→15:1) to obtain the title compound (4.94 g) having the following physical properties:

TLC: Rf 0.63 (ethyl acetate:hexane=1:2);
NMR (CDCl$_3$): δ 1.29 (t, J=7.1 Hz, 3H), 2.50-2.71 (m, 2H), 2.83 (t, J=7.2 Hz, 2H), 3.47 (s, 2H), 4.21 (q, 2H).

Example 3

6,7,7-trifluoro-6-heptene-1,3-diol (Compound 3)

A solution of compound 2 (4.71 g) in tert-butyl methyl ether (52 mL) was slowly added dropwise to boron lithium hydride (1.4 g) under ice cooling, followed by stirring at room temperature for 4 hr. The reaction solution was poured into a saturated aqueous solution of ammonium chloride under ice cooling and washed with ethyl acetate. The organic layer was washed with saturated brine; dried with sodium sulfate; and concentrated to obtain the title compound (3.87 g) having the following physical properties:

TLC: Rf 0.31 (ethyl acetate:hexane=2:1);
NMR (CDCl$_3$): δ 1.66-1.83 (m, 4H), 2.17-2.66 (m, 2H), 3.71-4.06 (m, 3H).

Example 4

6,7,7-trifluoro-1-[(1-phenyl-1H-tetrazol-5-yl)thio]-6-hepten-3-ol (Compound 4)

Compound 3 (3.87 g) was dissolved in toluene (50 mL) and a 2N aqueous solution of sodium hydroxide (50 mL), and tetrabutylammonium bromide (700 mg) and tosyl chloride chloride (4.10 g) were added thereto under ice cooling, followed by stirring for 30 min. To the reaction solution 1-phenyl-1H-tetrazole-5-thiol (4.60 g) was added, followed by stirring at 60° C. overnight. The reaction solution was poured into water and extracted with tert-butyl methyl ether. The organic layer was washed with saturated brine; dried with sodium sulfate; and concentrated. The resulting residue was purified by silica gel column chromatography (hexane:ethyl acetate=4:1→7:3) to obtain the title compound (5.43 g) having the following physical properties:

TLC: Rf 0.37 (ethyl acetate:hexane=2:1);

NMR (CDCl$_3$): δ 1.64-1.83 (m, 2H), 1.88-2.02 (m, 2H), 2.31-2.61 (m, 2H), 3.34-3.88 (m, 3H), 7.46-7.69 (m, 5H).

Example 5

6,7,7-trifluoro-1-[(1-phenyl-1H-tetrazol-5-yl)thio]-6-hepten-3-one (Compound 5)

Potassium bromide (830 mg), 2,2,6,6-tetramethylpiperidine-1-oxyl (199 mg) and an aqueous solution of sodium hypochlorite (10%, 6.1 mL) were added to a acetonitrile solution (32 mL) of compound 4 (2.18 g) under ice cooling, followed by stirring for 2 hr. A saturated aqueous solution of sodium thiosulfate was added to the reaction solution at the same temperature, followed by extraction with ethyl acetate. The organic layer was washed with water and saturated brine; dried with anhydrous sodium sulfate; and concentrated to obtain the title compound (2.17 g) having the following physical properties:

TLC: Rf 0.50 (ethyl acetate:hexane=1:2);

NMR (CDCl$_3$): δ 2.48-2.77 (m, 4H), 3.14 (t, J=6.4 Hz, 2H), 3.57 (t, J=6.4 Hz, 2H), 7.54 (s, 5H).

Example 6

6,7,7-trifluoro-3-methyl-1-[(1-phenyl-1H-tetrazol-5-yl)thio]-6-hepten-3-ol (Compound 6)

A methyl magnesium bromide/diethyl ether solution (3.0 M, 4.2 mL) was added to an anhydrous tetrahydrofuran solution (22 mL) of compound 5 (2.17 g) at −78° C. The mixed solution was stirred for 30 min at the same temperature and for 30 min under ice cooling. A saturated aqueous solution of sodium hydrogen carbonate was added to the reaction solution under ice cooling, followed by extraction with ethyl acetate. The organic layer was washed with water and saturated brine; dried with anhydrous sodium sulfate; and concentrated. The resulting residue was purified by silica gel column chromatography (hexane:ethyl acetate=7:3) to obtain the title compound (1.88 g) having the following physical properties:

TLC: Rf 0.39 (ethyl acetate:hexane=1:2);

NMR (CDCl$_3$): δ 1.29 (s, 3H), 1.69-1.92 (m, 2H), 1.99-2.19 (m, 2H), 2.30-2.59 (m, 2H), 3.33-3.67 (m, 2H), 7.42-7.70 (m, 514).

Example 7

6,7,7-trifluoro-3-methyl-1-[(1-phenyl-1H-tetrazol-5-yl)sulfonyl]-6-hepten-3-ol (Compound 7)

Hexaammonium heptamolybdenum tetrahydrate (318 mg) and aqueous hydrogen peroxide (30%, 1.8 mL) were added to a methanol solution (26 mL) of compound 6 (1.84 g) under ice cooling, followed by stirring at room temperature overnight. A saturated aqueous solution of sodium thiosulfate was added to the reaction solution under ice cooling, followed by extraction with ethyl acetate. The organic layer was washed with water and saturated brine; dried with anhydrous sodium sulfate; and concentrated to obtain the title compound (2.0 g) having the following physical properties:

TLC: Rf 0.41 (ethyl acetate:hexane=1:2);

NMR (CDCl$_3$): δ 1.30 (s, 3H), 1.69-1.86 (m, 2H), 2.06-2.24 (m, 2H), 2.30-2.57 (m, 2H), 3.80-4.00 (m, 2H), 7.51-7.78 (m, 5H).

Example 8

1-phenyl-5-({6,7,7-trifluoro-3-methyl-3-[(trimethylsilyl)oxy]-6-hepten-1-yl}sulfonyl)-1H-tetrazole (Compound 8)

Imidazole (524 mg) and trimethylsilyl chloride (0.79 mL) were added to a solution of compound 7 (2.0 g) in dimethylformamide (11 mL) under ice cooling, followed by stirring at room temperature for 5 hr. The reaction solution was poured into water and extracted with ethyl acetate. The organic layer was washed with saturated brine; dried with anhydrous sodium sulfate; and concentrated. The resulting residue was purified by silica gel column chromatography (hexane:ethyl acetate=9:1) to obtain the title compound (2.16 g) having the following physical properties:

TLC: Rf 0.72 (ethyl acetate:hexane=1:2);

NMR (CDCl$_3$): δ 0.15 (s, 9H), 1.35 (s, 3H), 1.66-1.86 (m, 2H), 1.96-2.19 (m, 2H), 2.25-2.46 (m, 2H), 3.74-3.88 (m, 2H), 7.56-7.67 (m, 3H), 7.68-7.74 (m, 2H).

Example 9

Ethyl 2-({2-[(1R,2S,5S)-2-(acetyloxy)-5-formylcyclopentyl]ethyl}thio)-1,3-thiazole-4-carboxylate (Compound 9)

Triethylamine (3.7 mL) and sulfur trioxide•pyridine complex (1.7 g) were added to a dimethyl sulfoxide (4.0 mL)/ethyl acetate (8.0 mL) solution of ethyl 2-({2-[(1R,2S,5S)-2-(acetyloxy)-5-(hydroxymethyl)cyclopentyl]ethyl}thio)-1,3-thiazole-4-carboxylate (500 mg) (see compound 7 described in the pamphlet of International Publication No. WO 2006/129788) at 10° C., followed by stirring at room temperature for 30 min. To the reaction solution, 1 N hydrochloric acid was added, followed by extraction with ethyl acetate. The organic layer was washed with water and saturated brine; dried with anhydrous sodium sulfate; and concentrated to obtain the title compound (497 mg) having the following physical properties:

TLC: Rf 0.27 (hexane:ethyl acetate=2:1);

NMR (CDCl$_3$): δ 1.32-1.49 (m, 3H) 1.78-2.15 (m, 9H) 2.35-2.51 (m, 1H) 2.69-2.84 (m, 1H) 3.10-3.31 (m, 2H) 4.32-4.48 (m, 2H) 5.29-5.37 (m, 1H) 8.02 (s, 1H) 9.67 (d, J=2.74 Hz, 1H).

Example 10

Ethyl 2-{[2-((1R,2S,5R)-2-(acetyloxy)-5-{(1E)-7,8,8-trifluoro-4-methyl-4-[(trimethylsilyl)oxy]-1,7-octadien-1-yl}cyclopentyl)ethyl]thio}-1,3-thiazole-4-carboxylate (Compound 10)

A potassium hexamethyldisilazide/toluene solution (0.5 M, 4.8 mL) was slowly added dropwise to a 1,2-dimethoxyethane (8.0 mL) solution of compound 8 (1.13 g) at −78° C., followed by stirring at the same temperature for 30 min. To the reaction solution, a 1,2-dimethoxyethane solution (5.0 mL) of compound 9 (461 mg) in was slowly added dropwise at the same temperature. After string at the same temperature for 30 min, the temperature was raised to 0° C. A saturated aqueous solution of sodium hydrogen carbonate was added, followed by extraction with ethyl acetate. The organic layer was washed with water and saturated brine; dried with anhydrous sodium sulfate; and concentrated. The resulting residue was purified by silica gel column chromatography (hexane:ethyl acetate=8:1) to obtain the title compound (703 mg) having the following physical properties:

TLC: Rf 0.71 (ethyl acetate:hexane=1:2);
NMR (CDCl$_3$): δ 0.10 (s, 9H), 1.39 (t, J=7.1 Hz, 3H), 1.49-2.48 (m, 17H), 3.10-3.40 (m, 2H), 4.40 (q, J=7.1 Hz, 2H), 5.18-5.53 (m, 3H), 8.02 (s, 1H).

Example 11

2-[(2-{(1R,2S,5R)-2-hydroxy-5-[(1E)-7,8,8-trifluoro-4-hydroxy-4-methyl-1,7-octadien-1-yl]cyclopentyl}ethyl)thio]-1,3-thiazole-4-carboxylic acid (Compound 11)

To an ethanol solution (6.0 mL) of compound 10 (703 mg), 2 N aqueous solution of sodium hydroxide (2.4 mL) was added under ice cooling, followed by stirring at room temperature overnight. To the reaction solution, 1 N hydrochloric acid was added at the same temperature, followed by stirring for 30 min. Water was added to the reaction solution, followed by extraction with ethyl acetate. The organic layer was washed with saturated brine; dried with anhydrous sodium sulfate; and concentrated to obtain the title compound (538 mg) having the following physical properties:

TLC: Rf 0.21 (ethyl acetate:methanol=5:1);
NMR (CDCl$_3$): δ 1.19 (s, 3H), 1.32-1.50 (m, 2H), 1.61-1.92 (m, 4H), 1.94-2.56 (m, 8H), 2.81-2.99 (m, 1H), 3.49-3.67 (m, 1H), 4.56 (m, 1H), 5.27-5.62 (m, 2H), 8.08 (s, 1H).

Example 12

2-[(2-{(1R,2S,5R)-2-(acetyloxy)-5-[(1E)-7,8,8-trifluoro-4-hydroxy-4-methyl-1,7-octadien-1-yl]cyclopentyl}ethyl)thio]-1,3-thiazole-4-carboxylic acid (Compound 12)

Anhydrous acetic acid (0.33 mL) was added to a pyridine solution (6.0 mL) of compound 11 (538 mg) under ice cooling, followed by stirring at room temperature overnight. The reaction solution was poured into 1 N hydrochloric acid and extracted with ethyl acetate. The organic layer was washed with saturated brine; dried with anhydrous sodium sulfate; and concentrated to obtain the title compound (589 mg) having the following physical properties:

TLC: Rf 0.27 (ethyl acetate:methanol=5:1);
NMR (CDCl$_3$): δ 1.16-1.21 (m, 3H), 1.34-2.54 (m, 17H), 3.10-3.53 (m, 2H), 5.33-5.61 (m, 3H), 8.11 (s, 1H).

Example 13

(10S,12E,13aR,16S,16aR)-10-methyl-8-oxo-10-(3,4,4-trifluoro-3-buten-1-yl)-1,10,11,13a,14,15,16,16a-octahydro-2H,8H-7,4-(azeno)cyclopenta[j][1,5,7]oxadithiacyclopentadecin-16-yl acetate (low-polarity form: compound 13A)

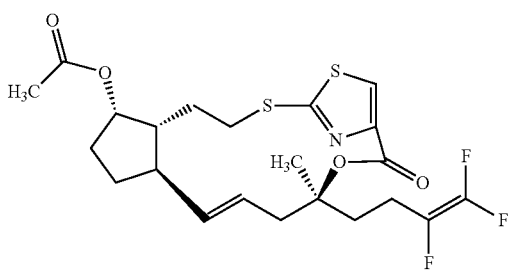 [SMILES: CC(=O)O[C@H]1CC[C@@H]2/C=C/C[C@](C)(CCC(F)=C(F)F)OC(=O)c3csc(n3)SCC[C@@H]12]

(10R,12E,13aR,16S,16aR)-10-methyl-8-oxo-10-(3,4,4-trifluoro-3-buten-1-yl)-1,10,11,13a,14,15,16,16a-octahydro-2H,8H-7,4-(azeno)cyclopenta[j][1,5,7]oxadithiacyclopentadecin-16-yl acetate (high-polarity form: compound 13B)

To a toluene solution (58 mL) of compound 12 (589 mg), 4,4-dimethylaminopyridine (567 mg) was added at room temperature. The reaction solution was heated to 100° C., and 2,4,6-trichlorobenzoyl chloride (0.37 mL) was added thereto. After stirring for 15 min, cooling to room temperature was carried out. The reaction solution was poured into a saturated aqueous solution of sodium hydrogen carbonate and extracted with ethyl acetate. The organic layer was washed with water and saturated brine; dried with anhydrous sodium sulfate; and concentrated. The resulting residue was purified by silica gel column chromatography (hexane:ethyl acetate=15:1) to obtain the title compounds (compound 13A: 200 mg, compound 13B: 120 mg) having the following physical properties: Compound 13A:

TLC: Rf 0.49 (ethyl acetate:hexane=1:4);
NMR (CDCl$_3$): δ 1.32-2.22 (m, 14H), 2.27-2.50 (m, 3H), 2.55-2.75 (m, 2H), 2.78-3.00 (m, 2H), 3.22-3.40 (m, 1H), 5.26-5.35 (m, 1H), 5.37-5.50 (m, 1H), 5.55-5.71 (m, 1H), 7.98 (s, 1H).

Compound 13B:
TLC: Rf 0.46 (ethyl acetate:hexane=1:4);
NMR (CDCl$_3$): δ 1.32-2.61 (m, 19H), 2.80-3.01 (m, 2H), 3.18-3.32 (m, 1H), 5.26-5.36 (m, 1H), 5.44-5.69 (m, 2H), 7.96 (s, 1H).

Example 14

2-[(2-{(1R,2S,5R)-2-hydroxy-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 14)

Compound 13A (200 mg) was dissolved in a mixed solvent of methanol (1.0 mL) and tetrahydrofuran (2.0 mL), and a 2 N aqueous solution of sodium hydroxide (0.62 mL) was added, followed by stirring at room temperature overnight. The reaction solution was poured into 1 N hydrochloric acid and extracted with ethyl acetate. The organic layer was washed with water and saturated brine; dried with anhydrous sodium sulfate; and concentrated to obtain the title compound (190 mg) having the following physical properties:

TLC: Rf 0.21 (ethyl acetate:methanol=5:1);

NMR (CDCl$_3$): δ 1.19 (s, 3H), 1.33-1.52 (m, 2H), 1.59-2.14 (m, 7H), 2.20 (d, J=6.6 Hz, 2H), 2.25-2.51 (m, 3H), 2.81-3.01 (m, 1H), 3.50-3.67 (m, 1H), 4.51-4.59 (m, 1H), 5.31-5.54 (m, 2H), 8.07 (s, 1H).

Example 15

Methyl 2-[(2-{(1R,2S,5R)-2-hydroxy-5-[(1E,4S)-7,8,8-trifluoro-4-hydroxy-4-methyl-1,7-octadien-1-yl]cyclopentyl}ethyl)thio]-1,3-thiazole-4-carboxylate (Compound 15)

Potassium carbonate (340 mg) and methyl iodide (0.09 mL) were added to a dimethylformamide solution (2.1 mL) of compound 14 (190 mg), followed by stirring at room temperature overnight. The reaction solution was poured into water and extracted with ethyl acetate. The organic layer was washed with water and saturated brine; dried with anhydrous sodium sulfate; and concentrated to obtain the title compound (196 mg) having the following physical properties:

TLC: Rf 0.36 (ethyl acetate:hexane=1:1);

NMR (CDCl$_3$): δ 1.18 (s, 3H), 1.29-1.49 (m, 2H), 1.53-1.88 (m, 4H), 1.91-2.11 (m, 3H), 2.19 (d, J=6.2 Hz, 2H), 2.27-2.52 (m, 3H), 2.82-2.97 (m, 1H), 3.50-3.68 (m, 1H), 3.92 (s, 3H), 4.42-4.53 (m, 1H), 5.30-5.51 (m, 2H), 7.98 (s, 1H).

Example 16

Methyl 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (Compound 16)

Diisopropylethylamine (0.43 mL) and sulfur trioxide·pyridine complex (196 mg) were added to a dimethyl sulfoxide (1.4 mL)/ethyl acetate (2.8 mL) solution of compound 15 (196 mg) under ice cooling, followed by stirring for 15 min. Water was added to the reaction solution, followed by extraction with ethyl acetate. The organic layer was washed with 1 N hydrochloric acid, water and saturated brine; dried with anhydrous sodium sulfate; and concentrated. The resulting residue was purified by silica gel column chromatography (hexane:ethyl acetate=3:2) to obtain the title compound (152 mg) having the following physical properties:

TLC: Rf 0.45 (ethyl acetate:hexane=1:1);

NMR (CDCl$_3$): δ 1.16 (s, 3H), 1.46-2.63 (m, 14H), 3.37-3.49 (m, 2H), 3.91 (s, 3H), 5.45-5.57 (m, 1H), 5.61-5.76 (m, 1H), 8.01 (s, 1H).

Example 17

2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid (Compound 17)

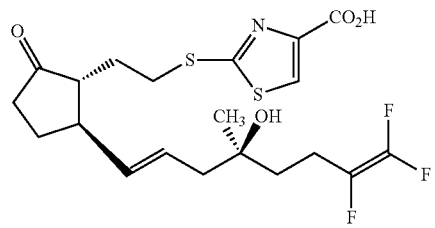 [SMILES: C[C@@](O)(C/C=C/[C@H]1CCC(=O)[C@@H]1CCSc1nc(C(=O)O)cs1)CCC(F)=C(F)F]

Compound 16 (152 mg) was dissolved in 1,2-dimethoxyethane (2.0 mL)/water (1.0 mL), and lithium hydroxide (16.0 mg) was added thereto under ice cooling, followed by stirring at room temperature for 2 hr. The reaction solution was poured into a 5% aqueous solution of potassium hydrogen sulfate and extracted with ethyl acetate. The organic layer was washed with water and saturated brine; dried with anhydrous sodium sulfate; and concentrated. The resulting residue was purified by silica gel column chromatography (hexane:ethyl acetate=1:1→methanol:ethyl acetate=1:10) to obtain the title compound (127 mg, amorphous, viscous oil) having the following physical properties:

TLC: Rf 0.20 (ethyl acetate:methanol=5:1);

NMR (CDCl$_3$): δ 1.21 (s, 3H), 1.55-1.80 (m, 3H), 1.88-2.60 (m, 11H), 3.37 (t, J=7.50 Hz, 2H), 5.54 (dd, J=14.82, 7.68 Hz, 1H), 5.62-5.76 (m, 1H), 8.11 (s, 1H).

Example 18

Piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (Compound 18)

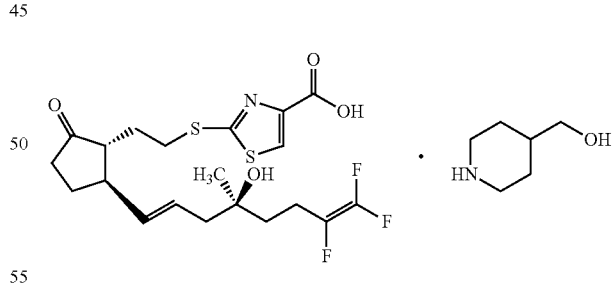

Compound 17 (7.0 g) was weighed in a 300 mL eggplant flask. After adding ethyl acetate (245 mL) thereto and dissolving Compound 17, 4-piperidinemethanol (1.744 g) was added and the solution was stirred overnight. The white crystal precipitated was collected by filtration and dried under reduced pressure, and the title compound (8.7 g, crude crystal) having the following physical properties was obtained.

TLC: Rf 0.18 (chloroform:methanol:water=60:10:1);

NMR (CD$_3$OD): δ 1.13 (s, 3H), 1.37-1.52 (m, 2H), 1.62-2.21 (m, 13H), 2.30-2.60 (m, 4H), 2.97 (dt, J=12.9, 3.0

Hz, 2H), 3.35-3.48 (m, 6H), 5.51 (dd, J=15.3, 8.1 Hz, 1H), 5.64 (dt, J=15.3, 6.9 Hz, 1H), 7.85 (s, 1H).

In this regard, it was found that this compound was a diastereomeric mixture from the NMR data above. Further, the compound was examined with using HPLC and the compound contained a diastereomer of Compound 18 in a ratio of about 9:1 (Compound 18:diastereomer).

Example 18(1)

Figure 2:
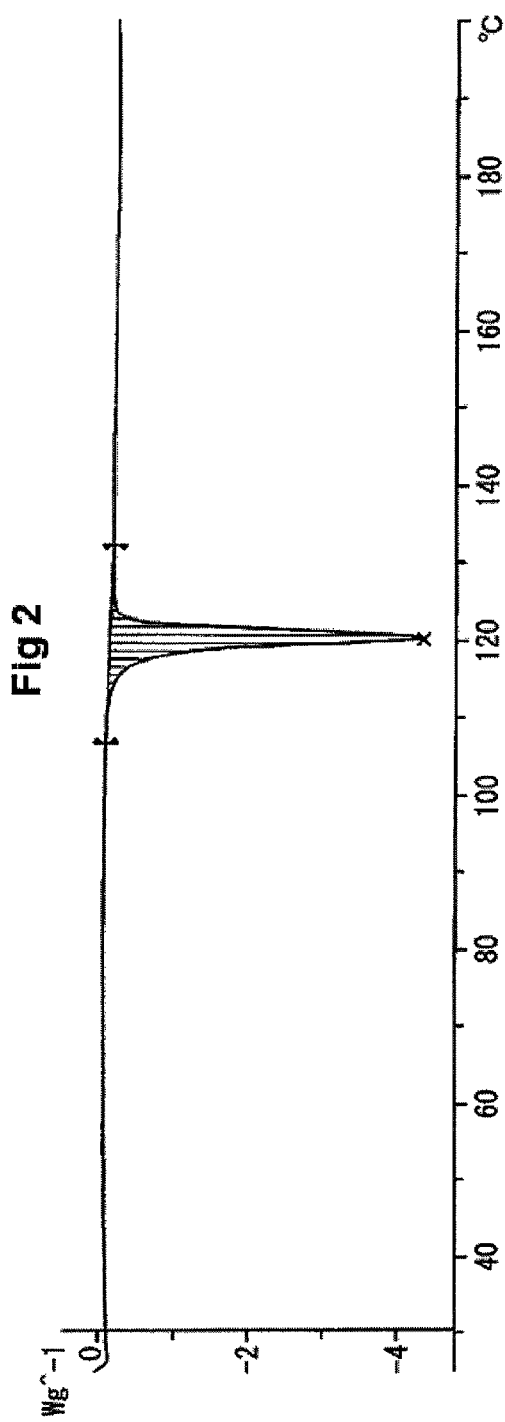
FIG. 2 shows the chart of differential scanning calorimetry of Crystalline form A of Compound 18.

Crystalline Form A of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate Compound 18 (60 mg) was weighed in a glass vial. After adding t-butyl methyl ether (300 µL) and isopropanol (300 µL) thereto and dissolving Compound 18 under heating at 40° C., the solution was stirred for 60 minutes. t-Butyl methyl ether (900 µL) was further added thereto and the solution was stirred under heating at room temperature for six hours. The slurry obtained was further stirred at 55° C. overnight. The slurry was collected by filtration and then dried at room temperature under reduced pressure and the title compound (30 mg, crystal) was obtained. The powder X-ray diffraction spectrum of the obtained crystal is shown in Table 2 and FIG. 1 below and the chart of differential scanning calorimetry is shown in FIG. 2. The onset of the endothermic peak of Crystalline form A of Compound 18 was 118° C.

TABLE 2

| Diffraction angle 2θ (°) | Relative intensity % |
|---|---|
| 9.05 | 78.4 |
| 9.44 | 85.9 |
| 12.61 | 36 |
| 13.96 | 33.6 |
| 15.57 | 24.6 |
| 16.82 | 34.4 |
| 17.45 | 29.5 |
| 18.09 | 66.1 |
| 18.91 | 90.5 |
| 19.42 | 48.2 |
| 20.53 | 100 |
| 21.77 | 62.9 |
| 22.60 | 33 |
| 23.38 | 37.3 |
| 24.59 | 51.2 |

Example 18(2)

Figure 3:
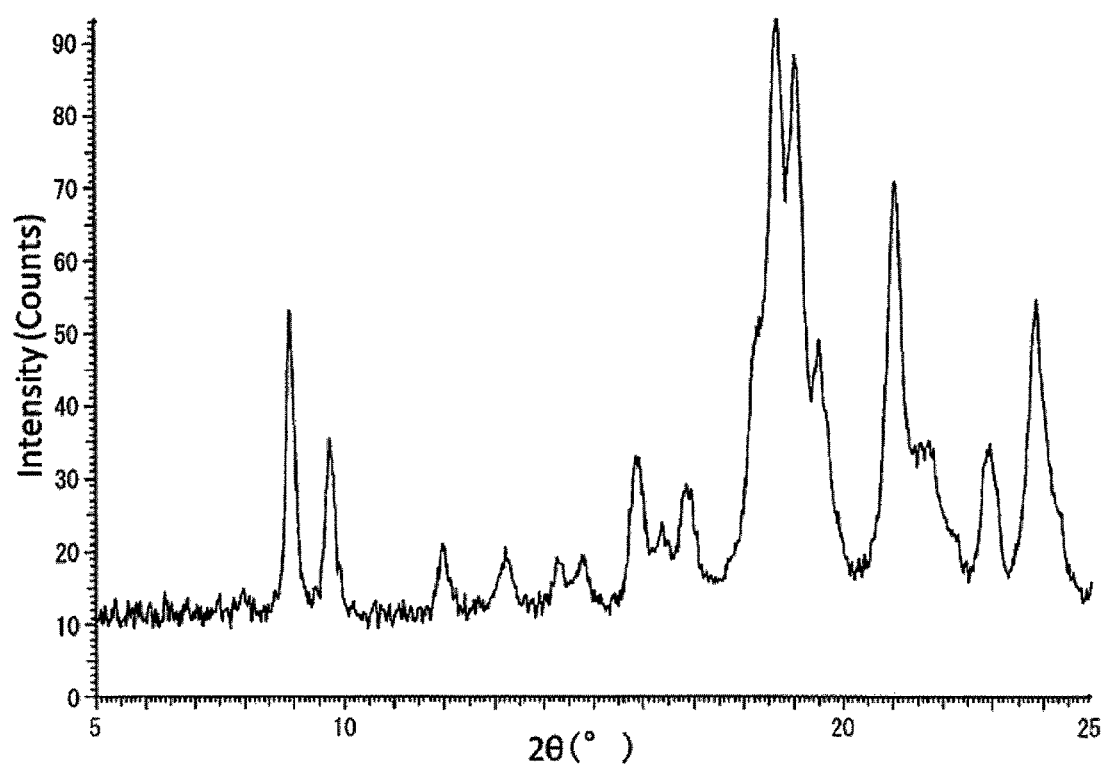
FIG. 3 shows the powder X-ray diffraction spectrum of Crystalline form B of Compound 18. The term "Intensity" in the figure means the diffraction intensity.
Figure 4:
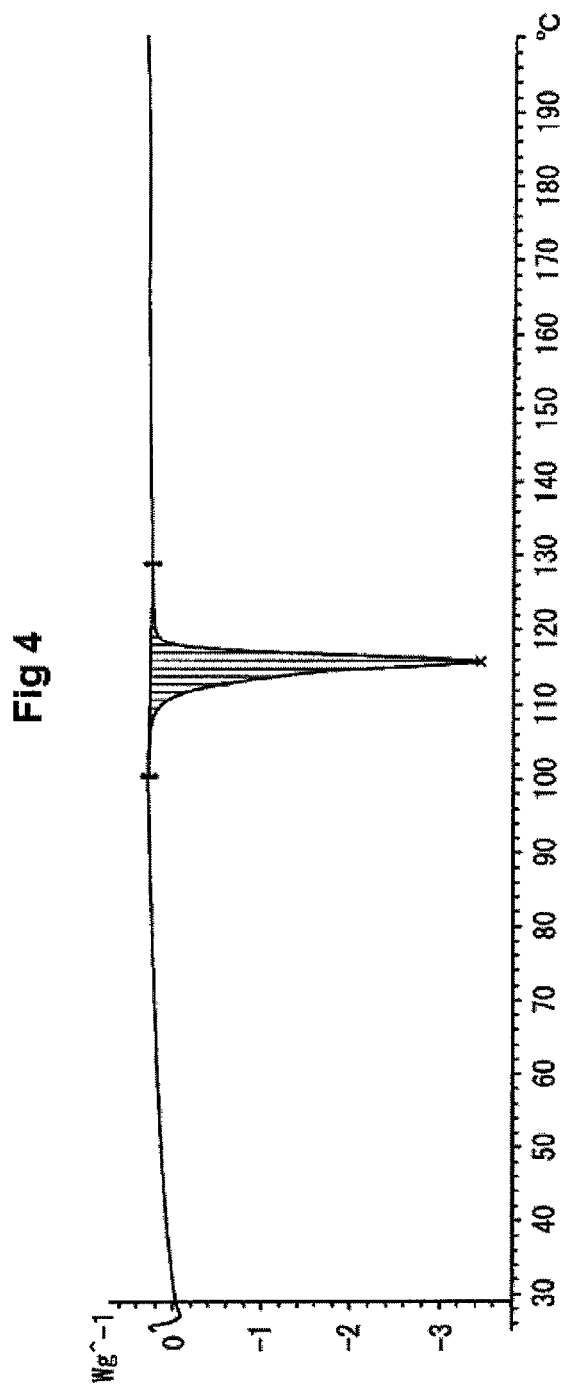
FIG. 4 shows the chart of differential scanning calorimetry of Crystalline form B of Compound 18.

Crystalline form B of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate Compound 18 (5.0 g) was weighed in a 200 mL eggplant flask. After adding ethyl acetate (50 mL) and isopropanol (12.5 mL) thereto and dissolving Compound 18 under heating at 60° C., the solution was stirred for 30 minutes. The solution was cooled to 0° C. and stirred overnight. The slurry obtained was collected by filtration and then dried at room temperature under reduced pressure and the title compound (4.6 g, crystal) was obtained. The powder X-ray diffraction spectrum of the obtained crystal is shown in Table 3 and FIG. 3 below and the chart of differential scanning calorimetry is shown in FIG. 4. The onset of the endothermic peak of Crystalline form B of Compound 18 was 113° C.

TABLE 3

| Diffraction angle 2θ (°) | Relative intensity % |
|---|---|
| 8.91 | 57 |
| 9.71 | 37.9 |
| 11.97 | 22.4 |
| 13.23 | 21.8 |
| 14.30 | 19.6 |
| 14.78 | 20.8 |
| 15.88 | 35.2 |
| 16.37 | 25.7 |
| 16.87 | 31.2 |
| 18.26 | 54.5 |
| 18.63 | 100 |
| 19.02 | 94.7 |
| 19.47 | 52.6 |
| 21.02 | 76 |
| 21.72 | 37.6 |
| 22.91 | 37.1 |
| 23.85 | 58.6 |

Example 18(3)

Crystalline form C of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate Compound 18 (50 mg) was weighed in a glass container. Tetrahydrofuran (50 mL) was added thereto and Compound 18 was dissolved under heating at 40° C. After leaving the solution still at 5° C. for 24 hours, the white crystal precipitated was collected by filtration and dried at room temperature under reduced pressure and thus a seed crystal (20 mg) of Crystalline form C was obtained.

Figure 5:
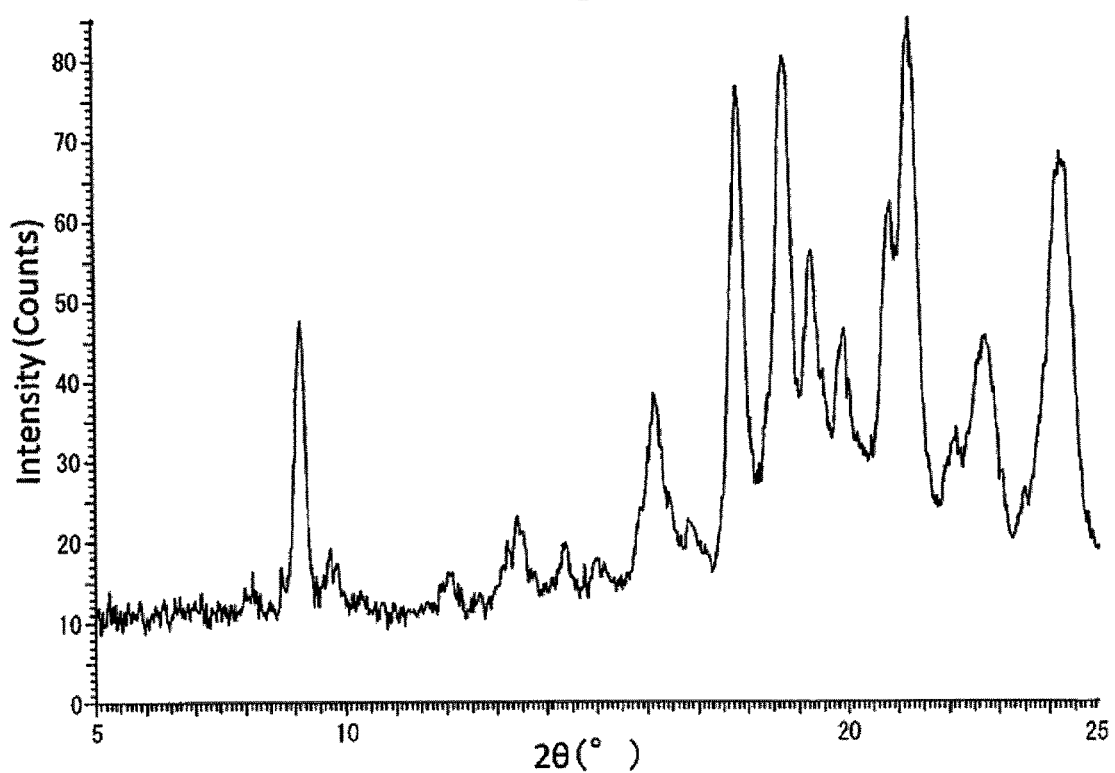
FIG. 5 shows the powder X-ray diffraction spectrum of Crystalline form C of Compound 18. The term "Intensity" in the figure means the diffraction intensity.
Figure 6:
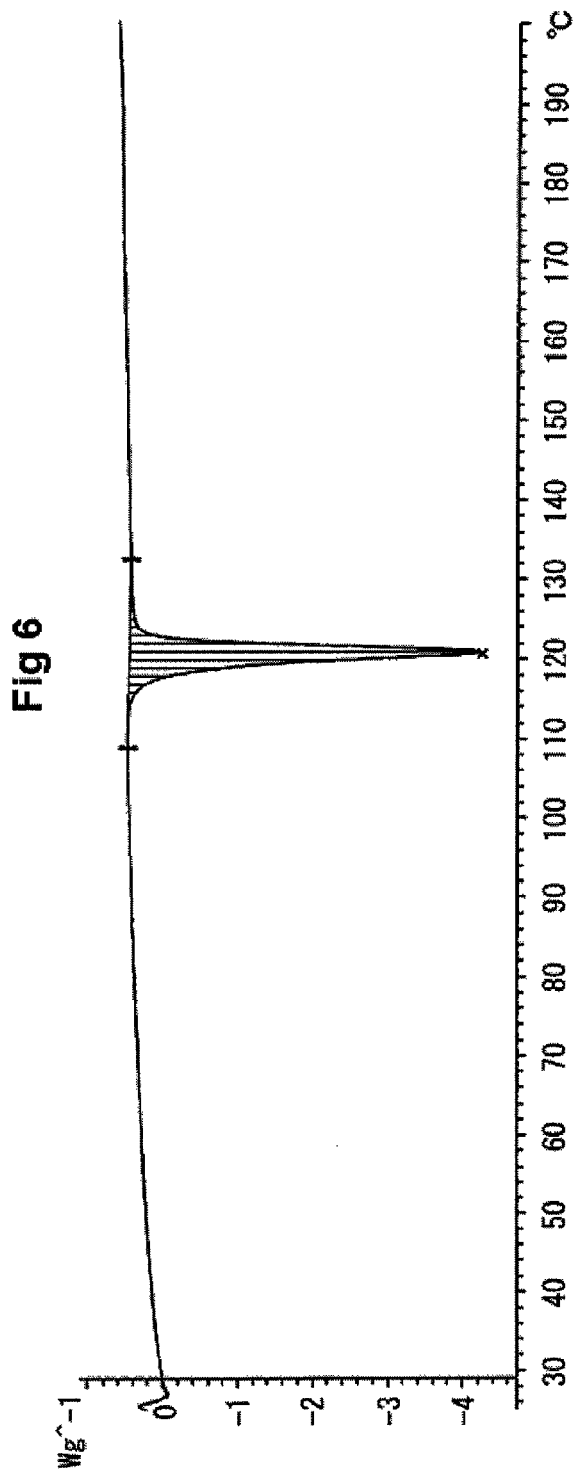
FIG. 6 shows the chart of differential scanning calorimetry of Crystalline form C of Compound 18.

Compound 18 (5.0 g) was weighed in a 200 mL eggplant flask. After adding tetrahydrofuran (50 mL) thereto and dissolving Compound 18 under heating at 45° C., the solution was stirred for 30 minutes. After cooling the solution to 0° C., the seed crystal above was added thereto and the solution was stirred overnight. To the slurry obtained, n-heptane (25 mL) was dropped and the solution was further stirred at 0° C. for five hours. After raising the temperature to room temperature, the slurry was collected by filtration and dried at room temperature under reduced pressure and the title compound (4.9 g, crystal) was obtained. The powder X-ray diffraction spectrum of the obtained crystal is shown in Table 4 and FIG. 5 below and the chart of differential scanning calorimetry is shown in FIG. 6. The onset of the endothermic peak of Crystalline form C of Compound 18 was 118° C.

TABLE 4

| Diffraction angle 2θ (°) | Relative intensity % |
|---|---|
| 8.12 | 19.2 |
| 9.11 | 55.6 |
| 9.72 | 22.4 |
| 12.06 | 18.7 |
| 13.43 | 25.9 |
| 14.38 | 23.2 |
| 14.97 | 20.8 |
| 16.16 | 44.8 |

TABLE 4-continued

| Diffraction angle 2θ (°) | Relative intensity % |
|---|---|
| 16.85 | 26.3 |
| 17.77 | 90 |
| 18.69 | 94.3 |
| 19.24 | 65.8 |
| 19.86 | 53.5 |
| 20.81 | 72.1 |
| 21.19 | 100 |
| 22.12 | 40 |
| 22.72 | 53.5 |
| 24.20 | 79.1 |

Example 19

β-Cyclodextrin clathrate of piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate (mixing molar ratio of 1:8)

Compound 18 (112.5 mg) and β-cyclodextrin (1.8 g) were weighed and dissolved in purified water (108 g). This solution (18.3 g) was weighed and dispensed into vials each in an amount of 600 μL. The vials were placed in a freeze drier (Triomaster type A04: manufactured by Kyowa Vacuum Engineering Co., Ltd) to freeze-dry the solution and the title compound was obtained.

The peaks derived from Compound 18
NMR ($D_2O$): δ 7.83 (s, 1H), 5.62-5.40 (m, 2H), 3.40-3.15 (m, 6H), 2.83 (dt, J=3.0, 13.2 Hz, 2H), 2.51 (m, 1H), 2.40-1.45 (m, 16H), 1.35-1.08 (m, 2H), 1.03 (s, 3H). The peaks derived from β-cyclodextrin
NMR ($D_2O$): δ 4.93 (d, J=3.9 Hz, 1H), 3.86-3.67 (m, 4H), 3.54-3.40 (m, 2H).

Example 20

Chemical Stability Test

With respect to Compound 17 and Crystalline forms A, B and C of Compound 18, chemical stability test was conducted according to the method and the condition below.
<Method>
In a laboratory tube, approximately 1.5 to 3 mg of a test compound was weighed and stored under the condition below.
After storing, the residual percentage (%) of the sample stored under each condition relative to the area percentage of the main component in the sample stored at −20° C. was calculated with using HPLC. In addition, the appearance was observed by eye and compared with the sample stored at −20° C.
<Storage Condition and Sampling Time>
  80° C.: One week, two weeks and one month
  60° C.: Two weeks and one month
  40° C.: Two weeks, one month, two months, four months and six months
  25° C.-60% RH: Two months, four months and six months
  5° C.: Two months, four months and six months
  40° C.-75% RH (opened): Two weeks, one month, two months, four months and six months
  25° C.-40% RH (opened): Two weeks, one month and two months
  25° C.-60% RH (opened): Two weeks, one month and two months
  25° C.-75% RH (opened): Two weeks, one month and two months
  2500 Lux: 10D, 20D
The samples to be compared with the samples above were stored at −20° C.
<HPLC Analysis>
Sample Preparation
  A sample to be evaluated was dissolved in a mixed solution of acetonitrile/20 mmol/L $KH_2PO_4$ aq. (pH3.0 with $H_3PO_4$) (1/1) and a solution of 1.0 mg/mL (concentration as a salt) was prepared.
Analysis Condition
  Detector: Ultraviolet absorptiometer (measurement wavelength: 215 nm)
  Column: CHIRALCEL OD-3R (150×4.6 mm, S-5 μm)
  Column temperature: 25° C.
  Mobile phase: Solution A: 20 mmol/L $KH_2PO_4$ aq. (pH3.0 with $H_3PO_4$), Solution B: $CH_3CN$
  Gradient condition: A/B=70130 (0 min)→40/60 (75-120 min)→70/30 (120-135 min)
  Flow rate: 0.5 mL/min
  Area measurement range: 35 minutes
  Charged amount: 10 μL
<Results>
The results are shown below.

TABLE 5

| | Residual percentage (%) | | | |
|---|---|---|---|---|
| | Compound 17 | Crystalline Form A | Crystalline Form B | Crystalline Form C |
| 60° C.-one month | 60.4 | 98.6 | 98.3 | 97.9 |
| 40° C.-one month | 76.0 | 99.6 | 99.6 | 99.4 |
| 40° C.-75% RH-one month | 58.6 | 92.0 | 92.6 | 97.5 |

During storage under each condition, the residual percentages of Compound 17, which is amorphous, decreased and Compound 17 was unstable. On the other hand, the residual percentages of Compound 18, which is a crystalline solid, were 90% or more in all the crystalline forms and these compounds were chemically very stable.

BIOLOGICAL EXAMPLES (1) Evaluation of the Activity to Contract the Bladder Detrusor <Construction of Incised Specimens>
Rats were anesthetized with pentobarbital, followed by abdominal incision to remove the bladders and the urethras. The bladder bodies were cut in the longitudinal direction to prepare strip specimens with a size of about 10×3 mm. Additionally, each of the urethras was also cut in the longitudinal direction to prepare specimens with a size of about 10×3 mm. The prepared specimens were suspended in Krebs buffer (37° C., 5 mL), which was aerated with a mixed gas of 95% $O_2$ and 5% $CO_2$. The tension values of the specimens were measured using a Magnus system equipped with an isometric transducer and an amplifier, and the measured values were recorded on a computer via a data collection system.

<Effects of Compounds on Bladders>

The specimens were suspended with a load of about 0.5 g. More than 1 hr later, potassium chloride (100 mmol/L) was added and the maximal contraction response was observed. After washing with Krebs buffer, the specimens were suspended with a load of about 0.5 g for stabilization. A potassium chloride solution (7.5 mmol/L) was added to induce the contraction of the specimens. After the contraction-inducing response was stabilized, the test compound was added in a cumulative manner and the response was observed before and after the treatment with the drug. The change of tension (%) of a test compound of each concentration was calculated with setting the contraction evoked by the addition of potassium chloride solution (mg) at 100%.

<Results>

The results are shown below.

TABLE 6

| | Change of tension (%) | | | |
|---|---|---|---|---|
| | 1 nmol/L | 10 nmol/L | 100 nmol/L | 1 μmol/L |
| Vehicle (n = 5) | 0.57 | 1.12 | −2.00 | 7.69 |
| Compound 18 (n = 3) | 5.97 | 54.35 | 177.91 | 245.91 |

The compound 18 contracted the bladder detrusor. Therefore, the compound of the present invention is effective for underactive bladder.

FORMULATION EXAMPLES

Formulation Example 1

The Crystalline form C of the compound 18 (5.0 g), calcium carboxymethyl cellulose (20 g), magnesium stearate (10 g) and microcrystalline cellulose (920 g) were mixed by a general method, followed by compression to produce 10,000 tablets wherein 0.5 mg of the active ingredient was present in each of the tablets.

Formulation Example 2

The Crystalline form A of the compound 18 (2.0 g), mannitol (500 g) and distilled water (10 L) were mixed by a general method, followed by sterilization by a general method. 1 mL of the solution was filled in a vial and frozen-dried by a general method. A total of 10,000 vials were obtained wherein 0.2 mg of the active ingredient was present in each of vials.

INDUSTRIAL APPLICABILITY

Since the compound of the present invention is a chemically very stable crystal, the compound can be stored for a long time and is very useful as a drug substance of medicaments.

In addition, since the compound of the present invention has an effect of contracting bladder detrusor and relaxing urethral sphincter, the compound ameliorates bladder contraction dysfunction and/or urethral relaxation dysfunction and is effective as an agent for preventing and/or treating underactive bladder. Furthermore, the compound is effective also as an agent for ameliorating various symptoms of underactive bladder. Thus, when the compound of the present invention, which is a stable crystal, is used as a drug substance and an oral preparation for long-term administration is produced, the preparation can be a highly effective therapeutic agent for underactive bladder.

The invention claimed is:

1. A salt of a compound represented by formula (I)

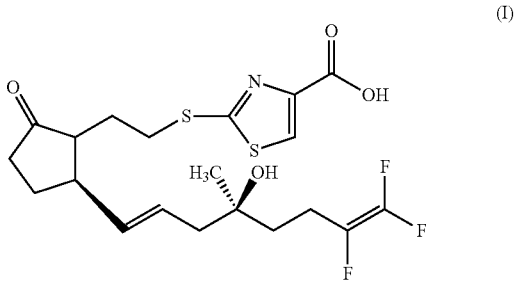 [SMILES: C[C@@](O)(C/C=C/[C@H]1CCC(=O)C1CCSc1nc(C(=O)O)cs1)CCC(F)=C(F)F]

wherein

⦚ represents an α-configuration,

▲ represents a β-configuration, and

╱ represents an α-configuration, a β-configuration or a mixture thereof in an arbitrary ratio, or a diastereomeric mixture thereof and 4-piperidinemethanol; a crystal thereof; or a cyclodextrin clathrate thereof.

2. The salt, the crystal thereof or the cyclodextrin clathrate thereof according to claim 1, wherein the compound represented by formula (I) is 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid.

3. The salt, the crystal thereof or the cyclodextrin clathrate thereof according to claim 1, wherein the compound represented by formula (I) is a diastereomeric mixture of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid.

4. The salt, the crystal thereof or the cyclodextrin clathrate thereof according to claim 3, wherein the diastereomer of 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid is 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylic acid.

5. Piperidin-4-ylmethanol 2-[(2-{(1R,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a diastereomeric mixture thereof, a crystal thereof or a cyclodextrin clathrate thereof.

6. Piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a crystal thereof or a cyclodextrin clathrate thereof.

7. A mixture of piperidin-4-ylmethanol 2-[(2-{(1R,5R)-2-oxo-5-[(1E,4S)-7,8, 8-trifluoro-4-hydroxy-4-methyl-1,7-octadien-1-yl]cyclopentyl}ethyl)thio]-1,3-thiazole-4-carboxylate and a diastereomer thereof: piperidin-4-ylmethanol 2-[(2-{(1S,5R)-2-oxo-5-[(1E,4S)-7,8,8-trifluoro-4-hydroxy-4-methyl-1,7-octadien-1-yl]cyclopentyl}ethyl)thio]-1,3-thiazole-4-carboxylate, a crystal thereof, or a cyclodextrin clathrate thereof.

8. A compound represented by formula (II)

(II)

wherein

⌀⌀⌀ represents an α-configuration,

▲ represents a β-configuration, and

／ represents an α-configuration, a β-configuration or a mixture thereof in an arbitrary ratio, a crystal thereof or a cyclodextrin clathrate thereof.

9. The salt of a compound of formula (I) and 4-piperidinemethanol according to claim 1 which is in the form of a crystal and has a crystalline form having 2θ peaks at least at approximately 9.05, 9.44, 12.61, 13.96 and 18.09° in a powder X-ray diffraction spectrum.

10. The salt of a compound of formula (I) and 4-piperidinemethanol according to claim 9 which has a crystalline form having 2θ peaks at least at approximately 9.05, 9.44, 12.61, 13.96, 18.09, 18.91, 19.42, 20.53, 21.77, 22.60, 23.38 and 24.59° in a powder X-ray diffraction spectrum.

11. The salt of a compound of formula (I) and 4-piperidinemethanol according to claim 1 which is in the form of a crystal and has a crystalline form having a substantially same powder X-ray diffraction spectrum as the powder X-ray diffraction spectrum shown in FIG. 1.

12. The salt of a compound of formula (I) and 4-piperidinemethanol according to claim 9 which has a crystalline form having an onset of an endothermic peak at approximately 118° C. in differential scanning calorimetry.

13. The salt of a compound of formula (I) and 4-piperidinemethanol according to claim 9 which has a crystalline form having the chart of differential scanning calorimetry shown in FIG. 2.

14. The salt of a compound of formula (I) and 4-piperidinemethanol according to claim 1 which is in the form of a crystal and has a crystalline form having 2θ peaks at least at approximately 8.91, 9.71, 11.97, 13.23 and 15.88° in a powder X-ray diffraction spectrum.

15. The salt of a compound of formula (I) and 4-piperidinemethanol according to claim 14 which has a crystalline form having 2θ peaks at least at approximately 8.91, 9.71, 11.97, 13.23, 15.88, 18.63, 19.02, 21.02, 22.91 and 23.85° in a powder X-ray diffraction spectrum.

16. The salt of a compound of formula (I) and 4-piperidinemethanol according to claim 1 which is in the form of a crystal and has a crystalline form having a substantially same powder X-ray diffraction spectrum as the powder X-ray diffraction spectrum shown in FIG. 3.

17. The salt of a compound of formula (I) and 4-piperidinemethanol according to claim 14 which has a crystalline form having an onset of an endothermic peak at approximately 113° C. in differential scanning calorimetry.

18. The salt of a compound of formula (I) and 4-piperidinemethanol according to claim 14 which has a crystalline form having the chart of differential scanning calorimetry shown in FIG. 4.

19. The salt of a compound of formula (I) and 4-piperidinemethanol according to claim 1 which is in the form of a crystal and has a crystalline form having 2θ peaks at least at approximately 9.11, 13.43, 16.16, 17.77 and 18.69° in a powder X-ray diffraction spectrum.

20. The salt of a compound of formula (I) and 4-piperidinemethanol according to claim 19 which has a crystalline form having 2θ peaks at least at approximately 9.11, 13.43, 16.16, 17.77, 18.69, 19.24, 19.86, 21.19, 22.72 and 24.20° in a powder X-ray diffraction spectrum.

21. The salt of a compound of formula (I) and 4-piperidinemethanol according to claim 1 which is in the form of a crystal and has a crystalline form having a substantially same powder X-ray diffraction spectrum as the powder X-ray diffraction spectrum shown in FIG. 5.

22. The salt of a compound of formula (I) and 4-piperidinemethanol according to claim 19 which has a crystalline form having an onset of an endothermic peak at approximately 118° C. in differential scanning calorimetry.

23. The salt of a compound of formula (I) and 4-piperidinemethanol according to claim 19 which has a crystalline form having the chart of differential scanning calorimetry shown in FIG. 6.

24. A pharmaceutical composition containing as an active ingredient: a salt of a compound represented by formula (I)

(I)

wherein

⌀⌀⌀ represents an α-configuration,

▲ represents a β-configuration, and

／ represents an α-configuration, a β-configuration or a mixture thereof in an arbitrary ratio, or a diastereomeric mixture thereof and 4-piperidinemethanol; a crystal thereof; or a cyclodextrin clathrate thereof.

25. A pharmaceutical composition containing the salt of a compound of formula (I) and 4-piperidinemethanol according to claim 9.

26. A method for contracting bladder detrusor and relaxing urethral sphincter, comprising administering an effective amount of the pharmaceutical composition according to claim 24 to a subject in need thereof.

27. A method for treating and/or ameliorating bladder contraction dysfunction and/or urethral relaxation dysfunction, comprising administering an effective amount of the pharmaceutical composition according to claim 24 to a subject in need thereof.

28. The method according to claim 27, wherein the bladder contraction dysfunction and/or the urethral relaxation dysfunction are underactive bladder.

* * * * *